(12) United States Patent
Belkhir et al.

(10) Patent No.: US 10,849,832 B2
(45) Date of Patent: Dec. 1, 2020

(54) CUSTOM FORMULATION SYSTEMS

(71) Applicant: L'OREAL, Paris (FR)

(72) Inventors: Yazid Belkhir, La Plaine Saint-Denis (FR); Frédéric Carlier, Clichy (FR); Laurent Bourdelain, Echirolles (FR)

(73) Assignee: L'OREAL, Paris (FR)

( * ) Notice: Subject to any disclaimer, the term of this patent is extended or adjusted under 35 U.S.C. 154(b) by 11 days.

(21) Appl. No.: 16/376,929

(22) Filed: Apr. 5, 2019

(65) Prior Publication Data

US 2020/0315926 A1 Oct. 8, 2020

(51) Int. Cl.
*A61K 8/00* (2006.01)
*A45D 44/00* (2006.01)
(Continued)

(52) U.S. Cl.
CPC ............... *A61K 8/00* (2013.01); *A45D 19/00* (2013.01); *A45D 44/005* (2013.01);
(Continued)

(58) Field of Classification Search
CPC .... A61K 8/00; A61K 2800/87; A45D 44/005; A45D 19/00; G06F 9/542; G06F 3/0482
(Continued)

(56) References Cited

U.S. PATENT DOCUMENTS 4,519,037 A    5/1985  Brodeur et al.
5,704,789 A *  1/1998  Yang ...................... B44C 3/123
                                                  221/185
(Continued)

FOREIGN PATENT DOCUMENTS

CN    205685961 U    11/2016
EP     0443741 B1     6/1995
(Continued)

OTHER PUBLICATIONS

International Search Report and Written Opinion, dated Jul. 31, 2020, issued in corresponding International Application No. PCT/EP2020/059528, filed Apr. 3, 2020, 12 pages.
(Continued)

*Primary Examiner* — Michael Collins
(74) *Attorney, Agent, or Firm* — Christensen O'Connor Johnson Kindness PLLC

(57) ABSTRACT

Custom formulation systems include a user input device and a dispenser having a cabinet, a bead assembly, a fluid formulation assembly, and a mixing area. The bead assembly dispenses a plurality of beads containing a first cosmetic formulation, and is one of a plurality of bead assemblies located within the cabinet. The plurality of bead assemblies has a vertically organized configuration. The fluid formulation assembly is configured to dispense a second cosmetic formulation in flowable fluid form, and is one of a plurality of fluid formulation assemblies located within the cabinet. The mixing area is located within the cabinet and configured to receive at least one bead from the bead assembly and the second cosmetic formulation in flowable fluid form from the fluid formulation assembly. The vertically organized bead assemblies, the fluid formulation assemblies, and the mixing area are positioned adjacent to a first side of the cabinet.

20 Claims, 18 Drawing Sheets

US 10,849,832 B2
Page 2

(51) Int. Cl.
  *G06F 9/54* (2006.01)
  *G06F 3/0482* (2013.01)
  *A45D 19/00* (2006.01)
(52) U.S. Cl.
  CPC ............ *G06F 3/0482* (2013.01); *G06F 9/542* (2013.01); *A61K 2800/87* (2013.01)
(58) Field of Classification Search
  USPC ................................................ 700/231–244
  See application file for complete search history.

(56) References Cited

U.S. PATENT DOCUMENTS

| | | | |
|---|---|---|---|
| 5,773,296 | A | 6/1998 | Montalbano et al. |
| 6,330,341 | B1 | 12/2001 | Macfarlane et al. |
| 6,490,492 | B1 | 12/2002 | Fertig et al. |
| 6,707,929 | B2 | 3/2004 | Marapane et al. |
| 6,719,565 | B1 | 4/2004 | Saita et al. |
| 6,761,697 | B2 | 7/2004 | Rubinstenn et al. |
| 6,887,431 | B1 | 5/2005 | Vann et al. |
| 6,959,119 | B2 | 10/2005 | Hawkins et al. |
| 7,079,158 | B2 | 7/2006 | Lambertsen |
| 7,110,117 | B2 | 9/2006 | Grossinger et al. |
| 7,151,851 | B2 | 12/2006 | Ladjevardi |
| 7,304,739 | B2 | 12/2007 | Grossinger et al. |
| 7,324,668 | B2 | 1/2008 | Rubinstenn et al. |
| 7,437,344 | B2 | 10/2008 | Peyrelevade |
| 7,463,356 | B2 | 12/2008 | Grossinger et al. |
| 7,489,816 | B2 | 2/2009 | Ladjevardi |
| 7,508,508 | B2 | 3/2009 | Grossinger et al. |
| 7,523,018 | B2 | 4/2009 | Grossinger et al. |
| 7,634,103 | B2 | 12/2009 | Rubinstenn et al. |
| 7,877,294 | B2 | 1/2011 | Inzinna, Jr. |
| 7,963,303 | B2 | 6/2011 | Saranow et al. |
| 8,005,270 | B2 | 8/2011 | Roizen et al. |
| D657,703 | S | 4/2012 | Stegmann et al. |
| 8,336,582 | B2 | 12/2012 | Saranow |
| 8,393,358 | B2 | 3/2013 | Saranow |
| 8,393,363 | B2 | 3/2013 | Saranow et al. |
| 8,498,456 | B2 | 7/2013 | Legagneur et al. |
| 8,510,168 | B2 | 8/2013 | Pitsch |
| D689,386 | S | 9/2013 | Stegmann et al. |
| 8,538,094 | B2 | 9/2013 | Roizen et al. |
| 8,567,455 | B2 | 10/2013 | Saranow et al. |
| 8,577,750 | B2 | 11/2013 | Mourad et al. |
| 8,655,744 | B2 | 2/2014 | Mourad et al. |
| 8,744,927 | B1 | 6/2014 | Neill et al. |
| 8,884,980 | B2 | 11/2014 | Mallick et al. |
| 8,897,915 | B2 | 12/2014 | Saranow |
| D721,591 | S | 1/2015 | Hefetz et al. |
| 8,977,389 | B2 * | 3/2015 | Witchell ................. F04B 43/12 700/233 |
| D731,116 | S | 6/2015 | Hefetz et al. |
| D732,736 | S | 6/2015 | Hefetz et al. |
| 9,142,054 | B2 | 9/2015 | Mallick et al. |
| 9,149,108 | B2 | 10/2015 | Miller et al. |
| 9,177,336 | B2 | 11/2015 | Hjelm et al. |
| 9,205,283 | B2 | 12/2015 | Miklatzky et al. |
| 9,316,580 | B2 | 4/2016 | Landa et al. |
| 9,414,665 | B2 | 8/2016 | Saranow et al. |
| 9,504,306 | B2 | 11/2016 | Miller et al. |
| 9,524,605 | B2 | 12/2016 | Saranow et al. |
| 9,623,388 | B2 | 4/2017 | Saranow et al. |
| 9,631,978 | B2 | 4/2017 | Fertig et al. |
| 9,839,278 | B2 | 12/2017 | Saranow et al. |
| 9,844,687 | B2 | 12/2017 | Landa et al. |
| 9,877,569 | B2 | 1/2018 | Miller et al. |
| 9,919,278 | B2 | 3/2018 | Saranow et al. |
| 9,961,984 | B2 | 5/2018 | Witchell et al. |
| 10,648,993 | B2 * | 5/2020 | Ludicke ............... G06F 3/04883 |
| 2003/0013994 | A1 | 1/2003 | Rubinstenn et al. |
| 2003/0063102 | A1 | 4/2003 | Rubinstenn et al. |
| 2003/0064350 | A1 | 4/2003 | Rubinstenn et al. |
| 2003/0065525 | A1 | 4/2003 | Giacchetti et al. |
| 2003/0065578 | A1 | 4/2003 | Peyrelevade et al. |
| 2003/0065588 | A1 | 4/2003 | Rubinstenn |
| 2003/0216941 | A1 | 5/2003 | Verry |
| 2004/0122553 | A1 | 6/2004 | Phan et al. |
| 2004/0122782 | A1 | 6/2004 | Audousset et al. |
| 2004/0163188 | A1 | 8/2004 | Firkins et al. |
| 2005/0165705 | A1 | 7/2005 | Lauper et al. |
| 2005/0194403 | A1 | 9/2005 | Mink et al. |
| 2005/0211599 | A1 | 9/2005 | De La Mettrie et al. |
| 2005/0228538 | A1 | 10/2005 | Limburger |
| 2005/0251463 | A1 | 11/2005 | Nagai et al. |
| 2005/0256733 | A1 | 11/2005 | Nagai et al. |
| 2006/0197775 | A1 | 3/2006 | Neal |
| 2006/0124196 | A1 * | 6/2006 | Bartholomew ..... B01F 13/1069 141/100 |
| 2006/0149151 | A1 | 7/2006 | Ladjevardi et al. |
| 2006/0178904 | A1 | 8/2006 | Aghassian et al. |
| 2006/0223506 | A1 | 10/2006 | Daurensan et al. |
| 2007/0047761 | A1 | 3/2007 | Wasilunas et al. |
| 2007/0058858 | A1 | 3/2007 | Harville et al. |
| 2007/0222547 | A1 | 9/2007 | Stahle et al. |
| 2007/0239539 | A1 | 10/2007 | King et al. |
| 2008/0136811 | A1 | 6/2008 | Adedayo et al. |
| 2009/0272758 | A1 | 11/2009 | Karwacki, Jr. et al. |
| 2011/0247718 | A1 | 10/2011 | Samain |
| 2012/0320191 | A1 | 7/2012 | Meschkat |
| 2012/0234340 | A1 | 9/2012 | Firkins et al. |
| 2013/0033590 | A1 | 2/2013 | Yacoob et al. |
| 2013/0301947 | A1 | 11/2013 | Legagneur et al. |
| 2014/0094964 | A1 * | 4/2014 | Bartholomew ..... B01F 13/1063 700/233 |
| 2014/0216492 | A1 | 8/2014 | Magri Amaral et al. |
| 2014/0306982 | A1 | 10/2014 | Ollivier |
| 2014/0313302 | A1 | 10/2014 | Franke et al. |
| 2015/0052008 | A1 | 2/2015 | Campbell |
| 2015/0104796 | A1 * | 4/2015 | Goemann-Thoss ................. G01N 35/00871 435/6.12 |
| 2015/0257974 | A1 | 9/2015 | Demers et al. |
| 2015/0342515 | A1 | 12/2015 | Hutchings et al. |
| 2016/0112616 | A1 | 4/2016 | Bonifer et al. |
| 2016/0183664 | A1 | 6/2016 | Grez |
| 2016/0209272 | A1 | 7/2016 | Miklatzky et al. |
| 2016/0335711 | A1 | 11/2016 | Hickman et al. |
| 2016/0339274 | A1 | 11/2016 | Landa et al. |
| 2017/0038297 | A1 | 2/2017 | Miklatzky et al. |
| 2017/0156476 | A1 | 6/2017 | Miklatzky et al. |
| 2017/0176217 | A1 * | 6/2017 | Ludicke ........... G01N 35/00722 |
| 2017/0270679 | A1 | 9/2017 | Koven |
| 2017/0364739 | A1 | 12/2017 | Soare et al. |
| 2018/0040053 | A1 | 2/2018 | Robinson et al. |
| 2018/0040054 | A1 | 2/2018 | Robinson et al. |
| 2018/0075776 | A1 | 3/2018 | Heitmann et al. |
| 2018/0103743 | A1 | 4/2018 | McKenzie |

FOREIGN PATENT DOCUMENTS

| | | |
|---|---|---|
| EP | 2168877 A2 | 3/2010 |
| WO | 2015166340 A2 | 11/2015 |
| WO | 2017032637 A1 | 8/2016 |
| WO | 2017077498 A1 | 11/2016 |
| WO | 2017127784 A1 | 1/2017 |
| WO | 2017077498 A1 | 5/2017 |
| WO | 2018007353 A1 | 7/2017 |
| WO | 2018007354 A1 | 7/2017 |
| WO | 2018007357 A1 | 7/2017 |
| WO | 2018007358 A1 | 7/2017 |
| WO | 2018089371 A1 | 5/2018 |

OTHER PUBLICATIONS

International Search Report and Written Opinion, dated Aug. 10, 2020, issued in International Application No. PCT/EP2020/059524, filed Apr. 3, 2020, 13 pages.

International Search Report and Written Opinion, dated Aug. 10, 2020, issued in International Application No. PCT/EP2020/059533, filed Apr. 3, 2020, 12 pages.

(56) References Cited

OTHER PUBLICATIONS

Non-Final Office Action dated Jul. 22, 2020, issued in U.S. Appl. No. 16/376,888, filed Apr. 5, 2019, 12 pages.
Non-Final Office Action dated Jul. 23, 2020, issued in U.S. Appl. No. 16/376,916, filed Apr. 5, 2019, 10 pages.

* cited by examiner

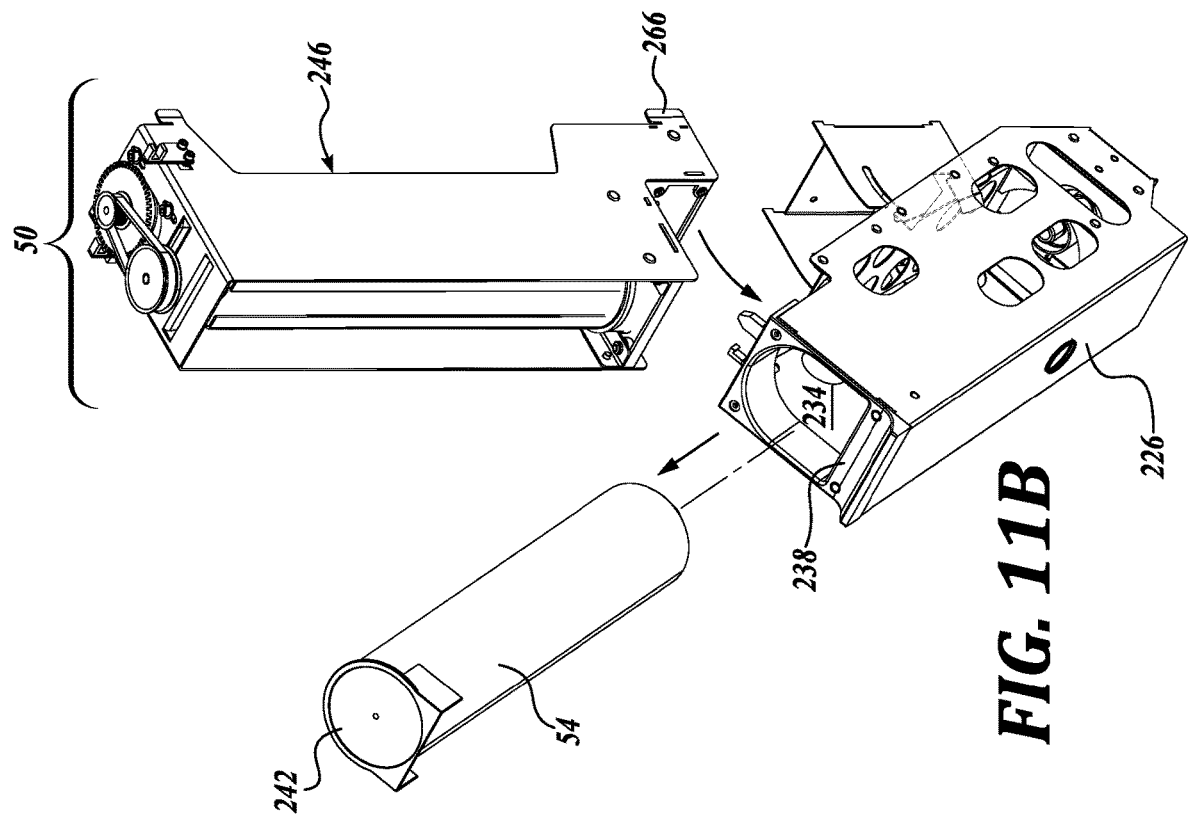
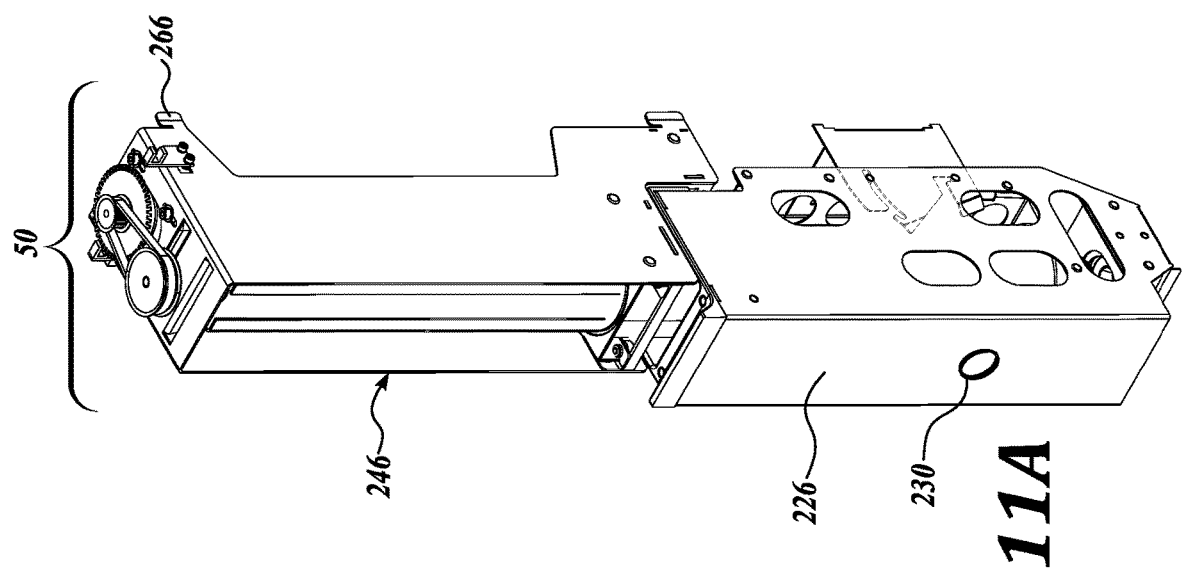

CUSTOM FORMULATION SYSTEMS

SUMMARY

The present disclosure generally provides systems and methods for creating custom hair formulations.

In an aspect, the present disclosure provides custom formulation systems that include a user input device and a dispenser. The dispenser includes a cabinet, a bead assembly, a fluid formulation assembly, and a mixing area. The bead assembly is configured to dispense a plurality of beads containing a first cosmetic formulation, and is one of a plurality of bead assemblies located within the cabinet. The plurality of bead assemblies has a vertically organized configuration in which one bead assembly is positioned gravitationally above at least one other bead assembly. The fluid formulation assembly is configured to dispense a second cosmetic formulation in flowable fluid form, and is one of a plurality of fluid formulation assemblies located within the cabinet. The mixing area is located within the cabinet and configured to receive at least one bead from the bead assembly and the second cosmetic formulation in flowable fluid form from the fluid formulation assembly. The plurality of vertically organized bead assemblies, the plurality of fluid formulation assemblies, and the mixing area are positioned adjacent to a first side of the cabinet.

In an embodiment, the bead assembly includes a modular bead unit containing the plurality of beads, and the modular bead unit is configured for removable attachment with the bead assembly without tools. In an embodiment, the bead assembly is configured for removable attachment with the dispenser without tools. In an embodiment, one bead assembly is positioned gravitationally above at least two other bead assemblies. In an embodiment, the plurality of bead assemblies also has a horizontally organized configuration. In an embodiment, the plurality of fluid formulation assemblies has a horizontally organized configuration. In an embodiment, the fluid formulation assembly is configured to receive one of a cartridge containing the second cosmetic formulation or a pouch containing the second cosmetic formulation. In an embodiment, the fluid formulation assembly is configured for removal and attachment with the dispenser without tools. In an embodiment, the dispenser includes a chute between the bead assembly and the mixing area. In an embodiment, the chute is configured to transport beads from a plurality of bead assemblies. In an embodiment, the bead assembly is one of a plurality of bead assemblies and the fluid formulation assembly is one of a plurality of fluid formulation assemblies. In an embodiment, each bead assembly and fluid formulation assembly is arranged in the dispenser in a common plane. In an embodiment, the custom formulation system includes a controller operatively connectable with the user input device, the bead assembly, and the fluid formulation assembly. In such embodiments, the controller is configured to receive information from the user input device, to instruct the bead assembly to dispense at least one bead, and to instruct the fluid formulation assembly to dispense the second cosmetic formulation. In an embodiment, the dispenser includes a climate control system operatively connected to the controller. In an embodiment, the user input device is integral with dispenser. In an embodiment, the bead assembly, fluid formulation assembly, and mixing area are contained within the dispenser. In an embodiment, the custom formulation system includes a tube configured to transfer fluid from the fluid formulation assembly to the mixing area. In an embodiment, the controller includes a processor and logic that, when executed, causes the system to perform operations. The operations include computing a target cosmetic formulation recipe based upon the information received from the user input device, dispensing a quantity of cosmetic formulation beads from the bead assembly, the quantity of cosmetic formulation beads being based upon the target cosmetic formulation recipe, and dispensing a volume of the second cosmetic formulation from fluid formulation assembly, the volume being based upon the target cosmetic formulation recipe. In an embodiment, the controller includes further logic that, when executed by the processor, causes at least one of the user input device or the dispenser to issue a notification when a bead supply of the bead assembly falls below a first threshold or when a fluid supply of the fluid formulation assembly falls below a second threshold.

In another aspect, the present disclosure provides a custom formulation dispenser having a cabinet, a bead assembly, a fluid formulation assembly, and a mixing area. The bead assembly is configured to dispense a plurality of beads containing a first cosmetic formulation, and is one of a plurality of bead assemblies located within the cabinet. The plurality of bead assemblies has a vertically organized configuration in which one bead assembly is positioned gravitationally above at least one other bead assembly. The fluid formulation assembly is configured to dispense a second cosmetic formulation in flowable fluid form, and is one of a plurality of fluid formulation assemblies located within the cabinet. The mixing area is located within the cabinet and configured to receive at least one bead from the bead assembly and the second cosmetic formulation in flowable fluid form from the fluid formulation assembly. The plurality of vertically organized bead assemblies, the plurality of fluid formulation assemblies, and the mixing area are positioned adjacent to a first side of the cabinet.

In another aspect, the present disclosure provides a bead assembly for a formulation dispenser. The bead assembly has a bead container configured to store a plurality of formulation beads, a singulator assembly configured to regulate dispensation of the formulation beads from the bead container, a sub-frame configured to support the bead container and the singulator assembly. A modular bead unit includes the bead container and at least a portion of the singulator assembly, and is removably attachable to the sub-frame.

In an embodiment, the singulator assembly includes a singulator wheel and the modular bead unit includes the singulator wheel. In an embodiment, the singulator assembly includes a motor that engages the singulator wheel. In an embodiment, the motor is not part of the modular bead unit. In an embodiment, the sub-frame forms a cradle configured to receive the modular bead unit and to engage the modular bead unit with at least two engagement fingers. In an embodiment, the cradle is configured to slidably receive the modular bead unit. In an embodiment, the sub-frame includes an engagement element that is configured to releasably engage a main frame of the cosmetic formulation dispenser without tools. In an embodiment, the modular bead unit includes a bead sensor located within a mouth of the bead container. In an embodiment, the modular bead unit includes a housing configured to support the bead container and to house the singulator wheel. In an embodiment, the bead assembly includes a latch that is configured to releasably retain the modular bead unit within the cradle. In an embodiment, the modular bead unit includes a tracking device. In an embodiment, the tracking device is a radiofrequency identification device or a near field communication device. In an embodiment, the sub-frame includes a chute configured to transport beads away from the bead container. In an embodiment, the sub-frame supports an electrical interface configured to draw power from the cosmetic formulation dispenser.

In another aspect, the present disclosure provides a dispenser for dispensing a formulation, the dispenser including a bead assembly having a bead container configured to store a plurality of formulation beads, a singulator assembly configured to dispense the formulation beads from the bead container, and a sub-frame configured to support the bead container and the singulator assembly. The sub-frame is removably attachable to the dispenser. A modular bead unit includes the bead container and at least a portion of the singulator assembly, and is removably attachable with the sub-frame. In an embodiment, the sub-frame includes a plurality of engagement members configured to engage the dispenser. In an embodiment, the dispenser includes a main frame having a plurality of apertures, each aperture being sized to receive one engagement member of the bead assembly. In an embodiment, each engagement member includes a prong projecting away from the bead assembly.

In another aspect, the present disclosure provides a custom formulation system that includes a dispenser having a main frame, a plurality of bead assemblies configured to fit within the dispenser, each bead assembly having a bead container configured to store a plurality of formulation beads, a singulator assembly configured to regulate dispensation of the formulation beads from the bead container; and a sub-frame configured to support the bead container and the singulator assembly. The sub-frame is removably attachable with the main frame of the dispenser, and a modular bead unit includes the bead container and at least a portion of the singulator assembly and is removably attachable with the sub-frame. In an embodiment, the main frame of the dispenser is configured to support the plurality of bead assemblies in a common vertical plane.

In another aspect, the present disclosure provides a fluid formulation assembly for a formulation dispenser. The fluid formulation assembly includes a fluid container configured to store a volume of fluid cosmetic formulation, a drive assembly operatively connectable to the fluid container and configured to dispense the fluid cosmetic formulation, and a carriage that receives the fluid container and is configured to interface with the drive assembly. The fluid container is removably attachable with the carriage without tools and at least one of the drive assembly or the carriage is removably attachable with the cosmetic formulation dispenser.

In an embodiment, the fluid container is a pouch. In an embodiment, the drive assembly includes a cylinder housing a piston, the piston being connected with a motor and being configured to draw cosmetic formulation from the pouch. In an embodiment, the pouch includes a valve that prevents dispensation of fluid from the pouch unless the pouch is received by the carriage. In an embodiment, the carriage supports an electrical interface configured to draw power from the cosmetic formulation dispenser. In an embodiment, the carriage includes a hinged handle. In an embodiment, the carriage includes a plurality of paddles that abut the pouch when the pouch is received within the carriage. In an embodiment, the pouch includes a tracking device. In an embodiment, the tracking device is a radiofrequency identification device or a near field communication device. In an embodiment, the cylinder has an inlet and an outlet. In an embodiment, the inlet of the cylinder is connected with a first check valve and the outlet is connected with a second check valve. In an embodiment, the carriage is removably attachable with the cosmetic formulation dispenser via a plurality of engagement members. In an embodiment, the drive assembly includes a peristaltic pump. In an embodiment, the fluid container is a cartridge. In an embodiment, the drive assembly is removably attachable with the cosmetic formulation dispenser via a plurality of engagement members. In an embodiment, the carriage hingeably connects to the drive assembly.

In another aspect, the present disclosure provides a dispenser for dispensing a formulation. The dispenser includes a fluid formulation assembly having a fluid container configured to store a volume of fluid cosmetic formulation, a drive assembly operatively connectable to the fluid container and configured to dispense fluid from the fluid container, and a carriage that receives the fluid container and is configured to interface with the drive assembly. The fluid container is removably attachable with the carriage without tools and at least one of the drive assembly or the carriage is removably attachable with the dispenser. In an embodiment, the fluid formulation assembly is one of a plurality of fluid formulation assemblies, and the dispenser includes a main frame that supports the plurality of fluid formulation assemblies in a common vertical plane in operation.

In another aspect, the present disclosure provides a custom formulation system that includes a dispenser having a main frame and a fluid formulation assembly. The fluid formulation assembly has a fluid container configured to store a volume of fluid cosmetic formulation, a drive assembly operatively connectable to the fluid container and configured to dispense fluid from the fluid container, and a carriage that receives the fluid container and is configured to interface with the drive assembly. The fluid container is removably attachable with the carriage without tools and at least one of the drive assembly or the carriage is removably attachable with the main frame. In an embodiment, the fluid formulation assembly is one of a plurality of fluid formulation assemblies and the main frame supports the plurality of fluid formulation assemblies in a common vertical plane in operation.

In another aspect, the present disclosure provides a method for creating custom hair formulations. The method includes generating a first input set and a second input set, formulating a hair formulation recipe, displaying a predicted hair color on the user input device, and dispensing a hair formulation from a dispenser. The first input set is based upon a plurality of present hair state inputs received by a user input device of a hair formulation system. The second input set is based upon a target hair state input received by the user input device. Formulating the hair formulation recipe includes using a processor of the hair formulation system that is operatively connected to the user input device to formulate the hair formulation recipe based upon the first and the second input sets. The predicted hair color is based upon at least one present hair state inputs and the target hair state input.

In an embodiment, the first input set includes at least one input selected from the group consisting of: color, texture, thickness, nationality, age, damage, environmental conditions, dry, oily, normal, straight, curly, wavy, kinky, length, thin, coarse, treated, and gray. In an embodiment, the second input set includes a target hair color. In an embodiment, the second input set includes a plurality of inputs. In an embodiment, the method includes displaying a diagnostic on the user input device, the diagnostic being based upon at least one present hair state inputs and the target hair state input. In an embodiment, generating at least one of the first input sets or the second input sets includes communicating with a digital assist platform. In an embodiment, the method includes displaying on the user input device a menu of present hair state options. In an embodiment, the menu of present hair state options includes a present hair state representation. In an embodiment, the method includes displaying on the user input device a menu of target hair state options. In an embodiment, the menu of target hair state options includes a target hair state representation. In an embodiment, the target hair state representation is based upon a customer image. In an embodiment, formulating the hair formulation recipe includes using the processor to select an ingredient from the group consisting of: a dye, a developer, a lotion, a cream, and a diluter. In an embodiment, dispensing the hair formulation includes dispensing the ingredient into a mixing area. In an embodiment, formulating the hair formulation recipe includes using the processor to select at least two ingredients from the group consisting of: a dye, a developer, a lotion, a cream, and a diluter. In an embodiment, dispensing the hair formulation includes sensing a weight of the hair formulation in the mixing area and controlling dispensation of the hair formulation based upon the weight. In an embodiment, the method includes monitoring a formulation inventory stored in the dispenser using the processor. In an embodiment, the method includes transmitting a refill signal from the hair formulation system when the formulation inventory falls below a threshold. In an embodiment, the method includes regulating a humidity level in the dispenser.

In another aspect, the present disclosure provides a computer program product stored on a non-transitory computer-readable medium that includes instructions that, when executed, cause a processor to perform steps. The steps include generating a first input set, a second input set, a hair formulation recipe based upon the first and second input sets, and a predicted hair color representation. The first input set is based upon a plurality of present hair state inputs received by a user input device of a hair formulation system. The second input set is based upon a target hair state input received by the user input device. The predicted hair color representation is based upon at least one of the present hair state inputs and the target hair state input. The steps include instructing one of a formulation dispenser and a user input device to display the predicted hair color representation. The steps include instructing the formulation dispenser to dispense a hair formulation based upon the hair formulation recipe.

In another aspect, the present disclosure provides a custom formulation system that includes a user input device, a formulation dispenser operatively connected to the user input device, the formulation dispenser, and a computer program product stored on a non-transitory computer-readable medium located in the user input device or the formulation dispenser, that when executed by a processor, causes a processor to perform steps. The steps include generating a first input set based upon a plurality of present hair state inputs received by the user input device, a second input set based upon a target hair state input received by the user input device, a hair formulation recipe based upon the first and the second input sets, and a predicted hair color representation based upon at least one of the present hair state inputs and the target hair state input. The steps include instructing the formulation dispenser or the user input device to display the predicted hair color representation. The steps include instructing the formulation dispenser to dispense a hair formulation based upon the hair formulation recipe.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the claimed subject matter will become more readily appreciated by reference to the following detailed description, when taken in conjunction with the accompanying drawings, wherein:

FIGS. 11A and 11B are isometric views of a cartridge assembly of the dispenser of FIG. 2, shown in different positions, including with the cartridge of FIG. 10 exploded;

DETAILED DESCRIPTION

Figure 1:
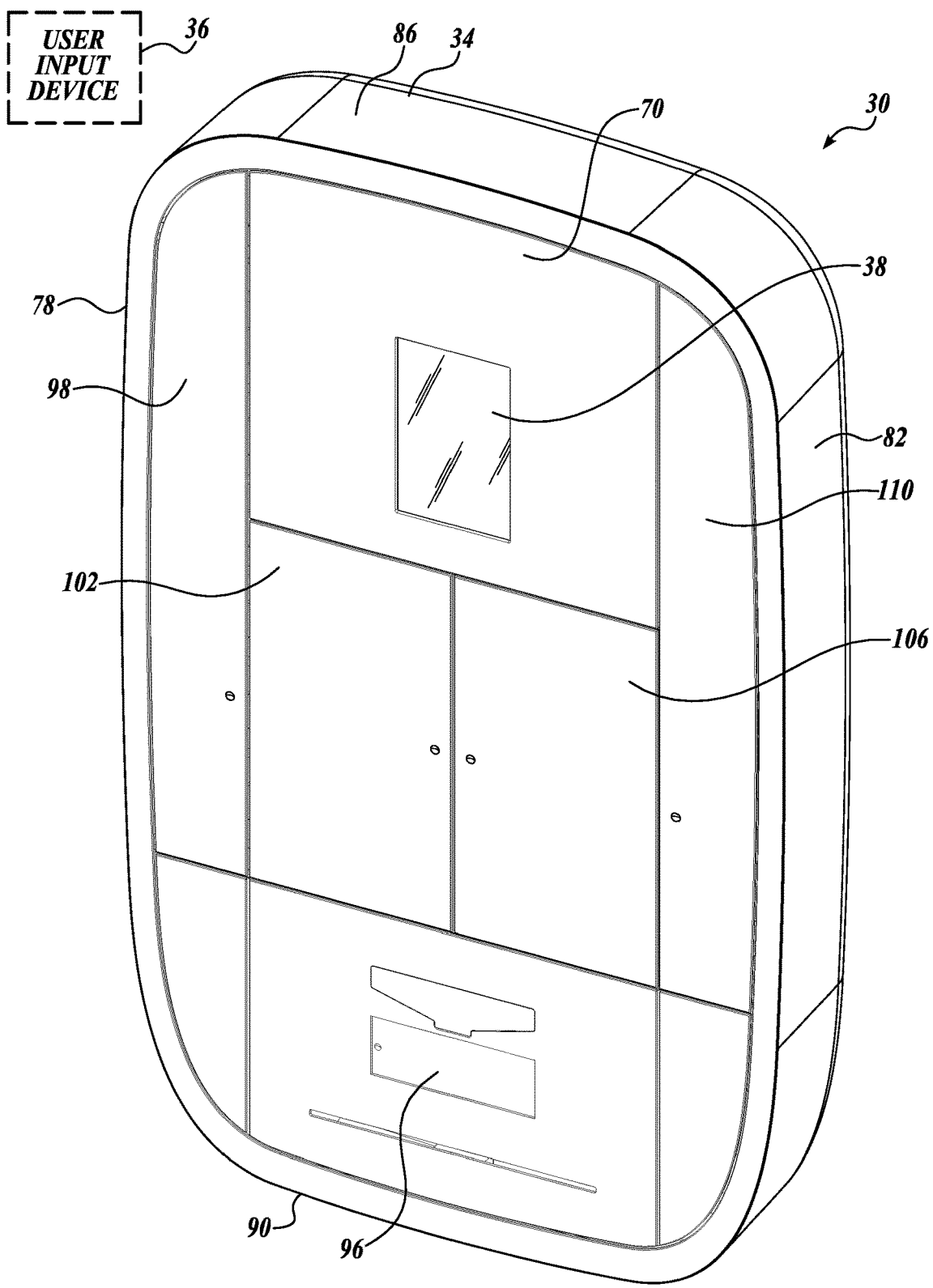
FIG. 1 is an isometric view of aspects of a custom formulation system formed in accordance with a representative embodiment of the present disclosure.

Application of a wide variety of treatment formulations to human hair and scalp tissue is a common practice. For instance, many people dye their hair to cover up or blend grey hair, to change the color of their hair, and/or to enhance the color of their hair with highlights, balayage, or the like (hereinafter, collectively referred to as "hair coloring", "hair dying," or the like). Hair dying with an at-home, hair coloring kit has several disadvantages, including difficulty of use, time consumption, uneven coverage, unpredictable results, excessive mess, etc. Accordingly, many people prefer to have their hair colored in a professional salon setting. The procedure for hair dying at a salon typically includes the following steps:

1. Hair diagnosis by a salon professional, where the customer's hair is analyzed and the desired outcome of the hair dying process is discussed with the customer;
2. Manual selection and retrieval of "color formulation" (including one or more dyes, developers, formulations, fluids, lotions, creams, diluters, etc., or any mixture thereof) by the salon processional;
3. Manual mixing of color formulation ingredients by the salon processional; and
4. Application of color formulation to customer's hair/scalp.

The second step, manual selection and retrieval of "color formulation" by the salon processional, can be time consuming, inaccurate, and inconsistent. Hair color formulation typically includes at least one dye and a separate developer, which must be mixed in controlled proportions for effective and predictable results.

The present disclosure provides examples of custom formulation systems (e.g., custom hair formulation systems) that automate at least a portion of the diagnosis and color formulation steps for a more efficient and accurate process and an improved overall customer experience. More specifically, the present disclosure generally describes examples of custom formulation systems suitable for automatically selecting and dispensing ingredients for hair color formulation. The custom formulation systems of the present disclosure provide a unique experience to each customer, such as by providing a personalized diagnostic, the selection and creation of a personalized formulation, and the dispensing of that personalized formulation.

Embodiments of the present disclosure may also be configured to dispense any suitable treatment formulations for the hair/scalp or other areas of the body. Examples of hair/scalp treatment formulations include: permanent hair dye; semi-permanent hair dye; developer; conditioner; hair growth treatment, such as minoxidil manufactured under the trade name ROGAINE®; hair protein treatment; disulfide bond repairing hair treatment; fluid hair treatment; fluid scalp treatment, and the like. Accordingly, the following discussion particularly refers to developers, formulations, fluids, lotions, creams, diluters, etc., combinations thereof, etc., as a non-limiting list of categories that include the above-identified examples.

Although any treatment formulation may be selected and dispensed using the embodiments of the custom formulation system described herein, the present disclosure generally refers to hair color formulation as the example of the treatment formulation dispensed by the dispenser described below. FIG. 1 illustrates a custom formulation system 30 (hereinafter referred to as a formulation system) formed in accordance with a representative embodiment of the present disclosure. The embodiment of FIG. 1 is non-limiting; the specific structures and functionalities of FIG. 1 are not limited to the illustrated embodiment, and may be practiced in whole or in part in other embodiments. The structural and functional features of the embodiment of FIG. 1 may be combined with functional and structural features of other embodiments (e.g., the embodiment of FIG. 13), and vice versa. Generally, the formulation system 30 includes a dispenser 34 and a user input device 36 that is configured to receive user inputs (such as through a touchscreen) and to communicate with the dispenser 34. The user input device 36 of FIG. 1 is shown as a tablet, but in other embodiments the user input device 36 may have a different form, including a mobile phone, a smartphone, a laptop or desktop computer, a controller, or a dedicated display that is integrated into the dispenser 34 or attachable (dockable) to the dispenser 34.

In an embodiment, the formulation system 30 includes a communications interface having circuits configured to enable communication with the user input device 36 via the internet, a Personal Area Network (PAN), Local Area Network, or a Wide Area Network. Accordingly, the communications interface is configured to communicate with the user input device 36 using standard wireless protocols (e.g., WIFI®, WIMAX®, BLUETOOTH®, ZIGBEE®, Cellular, Infrared, Nearfield, etc.) or wired protocols (Universal Serial Bus or other serial communications such as RS-234, RJ-45, etc., parallel communications bus, etc.). In an embodiment, the communications interface includes circuitry configured to initiate a discovery protocol that allows the user input device 36 and the formulation system 30 to identify each other and exchange control information. In an embodiment, the communications interface has circuitry configured to a discovery protocol and to negotiate one or more pre-shared keys. In an embodiment, the communications interface alternatively or additional includes circuitry configured to initiate a discovery protocol that allows an enterprise server and the formulation system 30 to exchange information. In an embodiment, the user input device 36 may be operatively connectable with one or more digital assist platforms to augment its functionality, including GOOGLE ASSISTANT®, AMAZON ALEXA®, or other digital assist platform.

In all cases, the user input device 36 is configured to transmit signals to and/or receive signals from the dispenser 34. To facilitate this connectivity, the user input device 36 may be operatively connected to a controller that is located within the dispenser 34. A more detailed description of the controller is described below with reference to FIG. 2. As used herein in the context of communications, operatively connected may include communicative, electromagnetic, magnetic, ultrasonic, optical, inductive, electrical, capacitive, and similar connections.

For example, the user input device 36 and the dispenser 34 may each include one or more of a transmitter, a receiver, a transceiver, or similar devices that may be configured to utilize one or more wireless communication standards, e.g., WIFI®, WIMAX®, BLUETOOTH®, ZIGBEE®, Cellular, Infrared, Near Field Communication (NFC), etc. or similar standards. Independently of the dispenser 34, the user input device 36 may include one or more processors (e.g., general processing units, graphical processing units, application specific integrated circuits); data stores; and modules that may be implemented as software logic (e.g., executable software code), firmware logic, hardware logic, or various combinations thereof.

As shown in FIG. 1, the dispenser 34 generally includes an optional dispenser interface 38, a controller 42, a plurality of bead assemblies 46 (e.g., 46a, 46b, 46c, 46d, etc.), and a plurality of fluid formulation assemblies—in this embodiment, cartridge assemblies 50 (e.g., 50a, 50b, 50c, etc.). The dispenser 34 in some embodiments is an electromechanical device that may be configured for electrical connection to a number of power sources, such as international standard "mains" voltages including but not limited to 110V AC, 120V AC, 127V AC, 220V AC, 230V AC, and 240V AC, or non "mains" sources such as batteries, fuel cells, etc. Accordingly, the dispenser 34 may include a power supply and additional electrical components in order to regulate and condition the power supplied to the dispenser. In an embodiment, the dispenser 34 includes circuitry having one or more modules optionally operable for communication with one or more input/output components that are configured to relay user output and/or input. In an embodiment, a module includes one or more instances of electrical, electromechanical, software-implemented, firmware-implemented, or other control devices. Such devices include one or more instances of memory; computing devices; antennas; power or other supplies; logic modules or other signaling modules; sensors, gauges or other such active or passive detection components; etc.

The optional dispenser interface 38 is a display that is integrated or attachable (dockable) with the dispenser 34, and is configured to display information (e.g., through an LCD screen) and may optionally receive user inputs (such as through a touchscreen). In the embodiment of FIG. 1, the dispenser interface 38 is operatively connected to the controller 42. In another embodiment, the dispenser interface 38 may be operatively connected to the controller 42 and/or the user input device. Like the user input device 36, the dispenser interface 38 may include one or more communication interfaces, processors (e.g., general processing units, graphical processing units, application specific integrated circuits); data stores; and modules that may be implemented as software logic (e.g., executable software code), firmware logic, hardware logic, or various combinations thereof. The dispenser interface 38 may be operatively connectable with one or more digital assist platforms to augment its functionality, including GOOGLE ASSISTANT®, AMAZON ALEXA®, or other digital assist platform. Some embodiments of the formulation system 30 may not include a dispenser interface 38, and in such embodiments the user input device 36 may have all or substantially all of the functionality of the dispenser interface 38. Likewise, some embodiments of the formulation system 30 may not include a user input device 36, and in such embodiments the dispenser interface 38 may have all or substantially all of the functionality of the user input device 36.

The controller 42 is operatively connected (e.g., via a wireless or wired connection) to the user input device 36 and to the dispenser interface 38, to each bead assembly 46, each cartridge assembly 50, and potentially to additional components (e.g., a load cell, a climate control device, and one or more lights or other indicators), and is configured to: receive information from the user input device 36, instruct the bead assembly 46 to dispense at least one bead based upon the information, and instruct the cartridge assembly 50 to dispense the a fluid based upon the information. The controller 42 may include one or more processors (e.g., general processing units, graphical processing units, application specific integrated circuits); data stores; and modules that may be implemented as software logic (e.g., executable software code), firmware logic, hardware logic, or various combinations thereof.

The controller 42, user input device 36, and/or the dispenser interface 38 may utilize external computing resources (e.g., cloud-based processing and storage systems such as AMAZON WEB SERVICES®) to execute the modules, which are described below. It will be appreciated that the user input device 36, dispenser interface 38, controller 42, etc., thereof, when executing one or more of the modules or implementing the technologies and methodologies described herein forms a special purpose user input device, dispenser interface, controller, processor, etc. Any of the electronic or electromechanical components described in this application may be connected directly or indirectly, either wired or wirelessly, to one or both of the user input device 36, dispenser interface 38, and controller 42.

Figure 2:
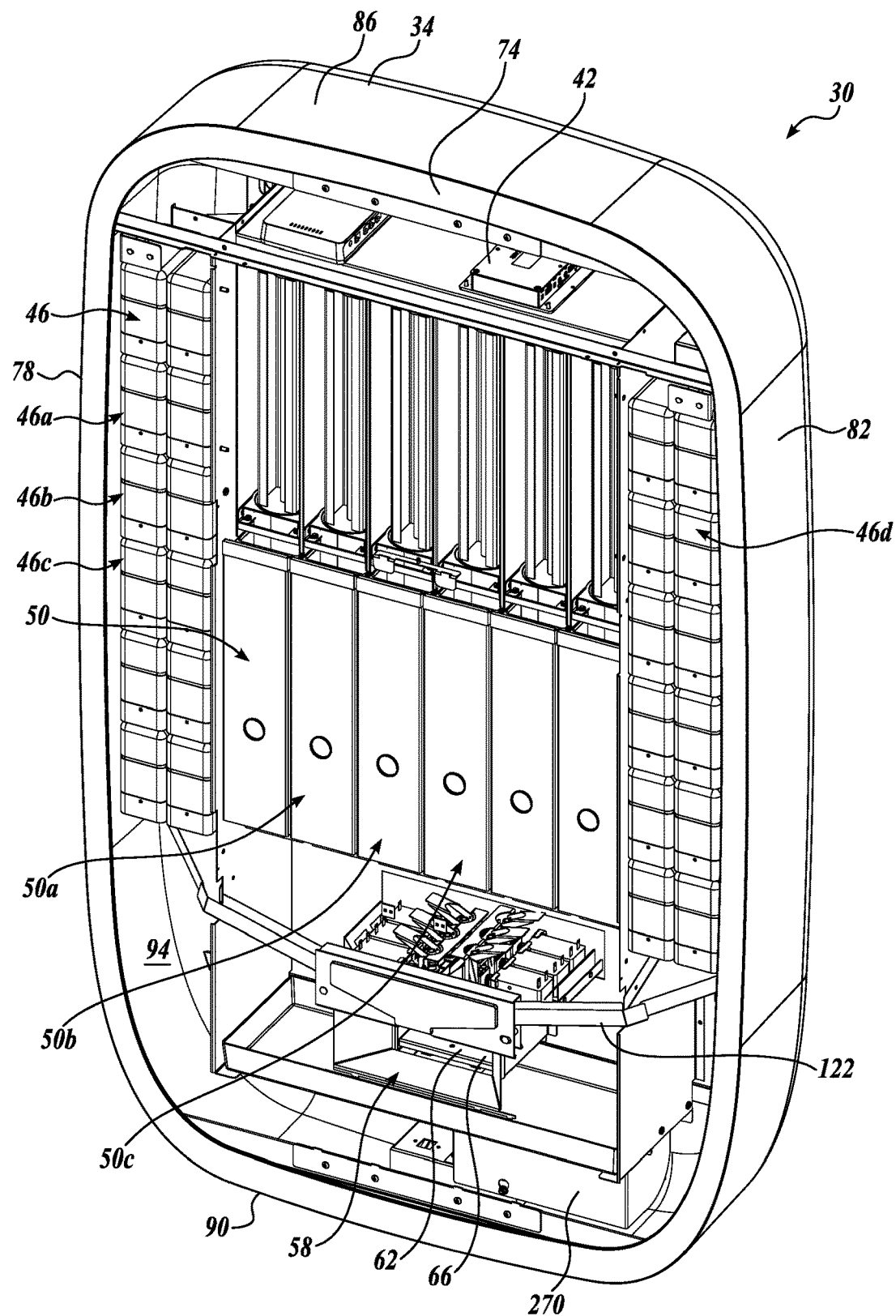
FIGS. 2 and 3 are front and rear isometric views, respectively, of one example of a dispenser of the custom formulation system of FIG. 1, showing portions of the dispenser removed to view the internal components.

Referring to FIG. 2, each bead assembly 46 is generally configured to contain a quantity of beads (e.g., beads of hair dye), while each cartridge assembly 50 is generally configured to contain one or more cartridges of fluids, e.g., developers, fluids, lotions, creams, diluters, etc. An exemplary bead is formed from a compacted powder, the powder having particular chemical properties. The bead is generally formulated to maintain its integrity within a range of environmental conditions, but to dissolve upon exposure to one or more chemicals (e.g., a cream) or to certain environmental conditions. The dispenser 34 may dispense the beads and the fluids in different quantities and combinations to produce numerous hair treatment formulations. Each bead assembly 46 and each cartridge assembly 50 is electrically connected to the controller 42, such that the controller 42 can cause one or more bead assemblies 46 and/or cartridge assemblies 50 to dispense beads and fluids, respectively, into a mixing area 58. The mixing area 58 may include a platform 62 and, for example, a sensor, such as load cell 66 (which may be integral to the platform 62), and the platform 62 may be configured to support a vessel such as a bowl. A technician may then mix the beads and fluids in the vessel to prepare the hair treatment formulation for application to the user's hair.

The dispenser 34 may be configured for mounting to a vertical surface (e.g., a wall) and/or for placement upon a horizontal surface (e.g., a floor or a table), such as via a stand or pedestal. The dispenser 34 may have a width w that ranges from about 50 cm to about 120 cm, e.g., about 60 cm, about 75 cm, about 80 cm, about 85 cm, about 90 cm, about 95 cm, about 100 cm, or any other value in that range. The dispenser 34 may have a height h that ranges from about 50 cm to about 120 cm, e.g., about 105 cm, about 110 cm, about 115 cm, or any other value in that range. The dispenser 34 may have a depth d that ranges from about 5 cm to about 50 cm, e.g., about 10 cm, about 20 cm, about 30 cm, or any other value in that range. Of course, other dimensions may be practiced with other embodiments of the present disclosure. The dispenser 34 may also have a particular form factor that lends itself to efficient use of space, ergonomics, or other advantage. Exemplary form factors include a ratio of the height h to width w of about 0.5 to about 5.0, for example about 0.75, about 1.0, about 1.5, about 1.75, or any other value in that range.

Figure 3:
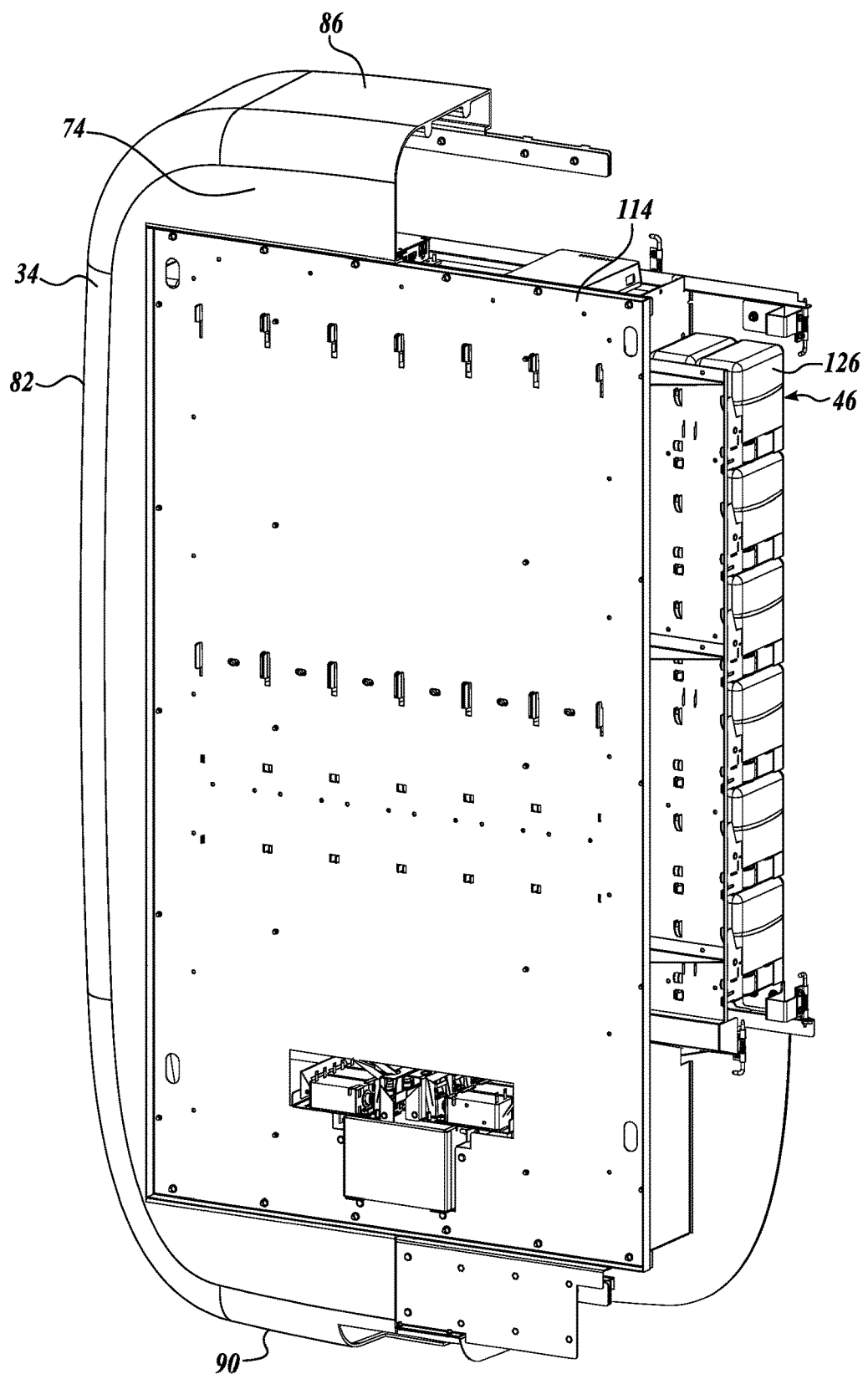

In the non-limiting embodiment shown in FIGS. 1, 2, and 3, the dispenser 34 includes a cabinet 35 with six sides, including a first side 70 (a front side), a second side 74 (a rear side—see FIG. 3), a third side 78 (a left side), a fourth side 82 (a right side), a fifth side 86 (a top side), and a sixth side 90 (a bottom side). The aforementioned sides are intended to orient the following discussion, and are not intended to limit the structure of each side. Each side may comprise one or more panels, doors, and/or other structures. Additionally, each side may have a different shape than is shown in FIGS. 1, 2, and 3. The sides of the cabinet 35 enclose an internal space 94 which may be partially or completely obscured from view during normal operation, and which may be relatively airtight under certain conditions, or at least limit the introduction of outside air into the cabinet 35. Any of the sides may be partially or completely removable, and/or may include one or more apertures, doors (e.g., doors having magnet strips to retain the doors in a closed position), or panels, such as to facilitate access to the internal space 94 and components contained within. For example, in the embodiment of FIG. 1, the first side 70 (the front side) includes a door 96 that is sized to receive a vessel that may be placed in the mixing area 58. The first side 70 (the front side) also includes an opening or recess where the dispenser interface 38 is integrated into the dispenser 34. The first side 70 (the front side) also includes a removable first panel 98 (a left outboard panel), a removable second panel 102 (a left inboard panel), a removable third panel 106 (a right inboard panel), and a removable fourth panel 110 (a right outboard panel) for accessing components contained within the internal space 94. Some embodiments may include fewer or more numerous panels, which may have different shapes and locations.

The non-limiting dispenser 34 shown in FIG. 2 contains a number, e.g., twenty-four, of bead assemblies 46 and a number, e.g., six, of cartridge assemblies 50. Some embodiments may include a fewer or greater number of bead assemblies 46 and/or cartridge assemblies 50, for example between 10 and 30 bead assemblies and/or cartridge assemblies, e.g., 10, 15, 20, 25, 30, or another number of bead assemblies and/or cartridge assemblies, all of which may fit within the dispenser 34. When the dispenser 34 is positioned for operation, the bead assemblies 46 and the cartridge assemblies 50 are located gravitationally above the mixing area 58. As shown in FIG. 3 and described in more detail below, each bead assembly 46 and each cartridge assembly 50 is structurally supported by a main frame 114 of the dispenser 34, and is configured to be removably attachable with the main frame 114 without tools. The main frame 114 may include one or more panels, sub-frames, or other structural elements. For example, the main frame 114 may include one or more sheet metal panels having openings that are configured to receive prongs or similar structure of the bead assemblies 46 and cartridge assemblies 50.

Referring again to FIG. 2, the bead assemblies 46 are configured in an array having vertically-organized and horizontally-organized aspects, while the cartridge assemblies 50 are configured in a horizontally-organized array. By "vertical," the present description refers to orientations where at least one unit (e.g., at least one bead assembly 46 or cartridge assembly 50) is located at least partially gravitationally above and at least partially over another similar unit when the dispenser 34 is positioned for operation. By "horizontal," the present description refers to orientations where at least one unit (e.g., at least one bead assembly 46 or cartridge assembly 50) is located next to (and not over) another similar unit when the dispenser 34 is positioned for operation. In the embodiment of FIG. 2, the vertical direction extends along (e.g., parallel to) the third side 78 and fourth sides 82 (the left and right sides). By comparison, the horizontal direction extends along (e.g., parallel to) the fifth side 86 and sixth side 90 (the top and bottom sides). In the embodiment of FIG. 2, the vertical direction may extend away from the mixing area 58.

With the foregoing orientation in mind, the bead assemblies 46 of FIG. 2 are arranged in, e.g., four vertical columns, each column having, e.g., six bead assemblies 46. Some embodiments may include a fewer or greater number of bead assemblies. Some embodiments may include bead assemblies having different orientations, or having different positions within the dispenser.

Figure 4:
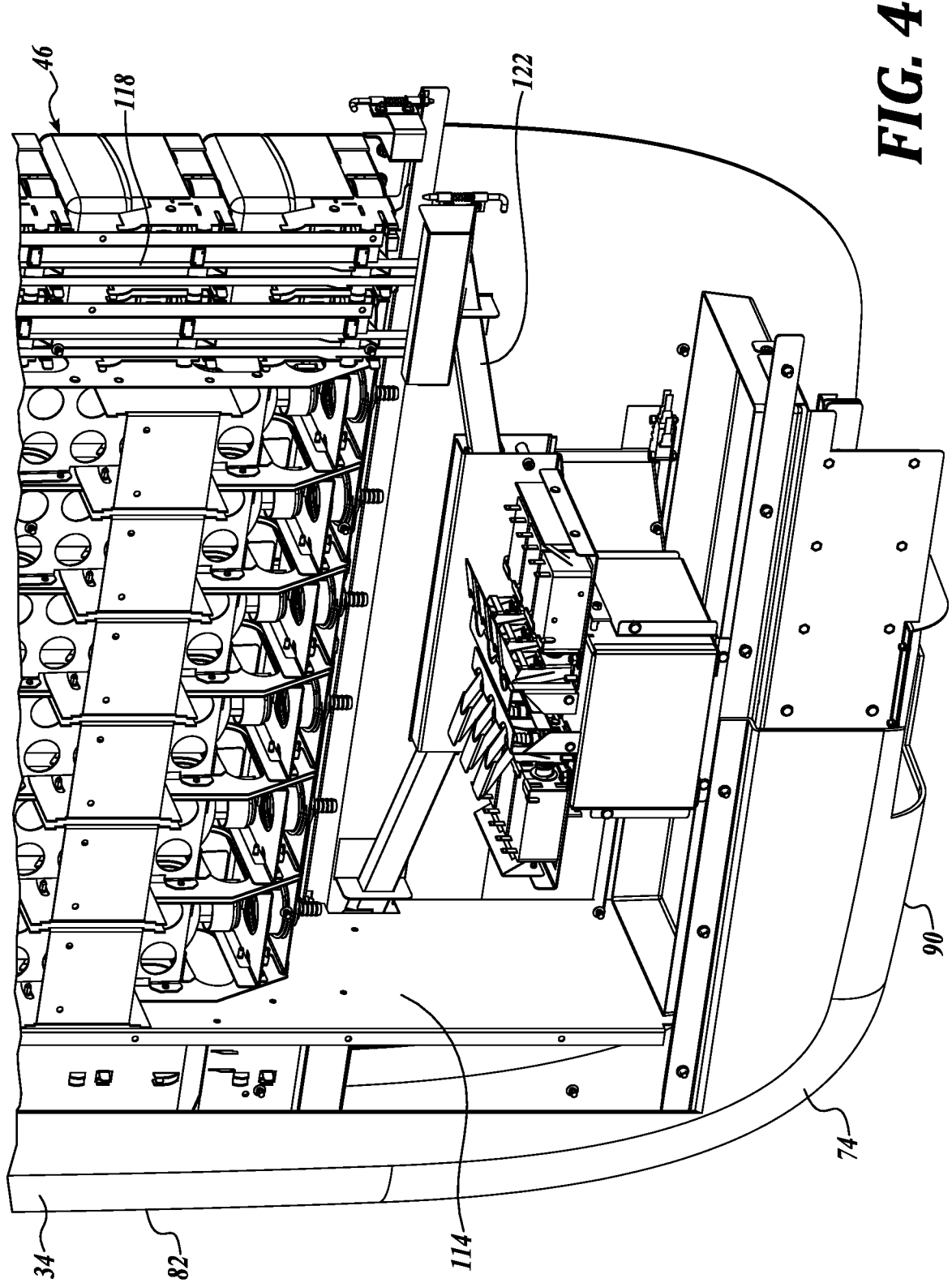
FIG. 4 is a partial rear isometric view of the dispenser of FIG. 2, showing portions of the dispenser removed to view the internal components.

FIG. 4 shows a partial rear view of the dispenser 34 with certain elements hidden. As shown in FIG. 4, each bead assembly 46 within each column is connected by a primary chute 118 that generally extends in the direction of the vertical column of bead assemblies 46 that it connects, e.g., the vertical direction. For example, the primary chute 118 shown in FIG. 4 extends away from the mixing area 58. In the embodiment of FIG. 4, the dispenser 34 includes four primary chutes 118 (though not all are visible)—one primary chute 118 for each vertical column of six bead assemblies 46. Some embodiments may include a different number of primary chutes, and each primary chute may be configured to receive beads dispensed from a different number of bead assemblies. In the embodiment of FIG. 4, the primary chute 118 is formed integrally with the main frame 114 of the dispenser 34, but may be a separate component in some embodiments. The primary chute 118 of FIG. 4 is linear, although in some embodiments, it may be non-linear. For example, in some embodiments, the primary chute may include one or more bends or corners designed to reduce a velocity with which beads free-fall down the primary chute. Each primary chute 118 may terminate gravitationally above and adjacent to an aggregator chute 122 (two are visible in FIG. 4), and each aggregator chute 122 terminates gravitationally above the mixing area 58. In operation, beads dispensed from each bead assembly 46 travel to the mixing area 58 via the primary chute 118 and the aggregator chute 122, e.g., by gravity.

Referring again to FIG. 2, the cartridge assemblies 50 are arranged in a single horizontal row that is positioned in between the vertical columns of bead assemblies 46. Some embodiments may include fewer or greater cartridge assemblies. Some embodiments may include cartridge assemblies having different orientations, or having different positions within the dispenser. For example, some embodiments may include cartridge assemblies arranged in a vertical array; in such embodiments, each cartridge assembly may include a tube, channel, or similar structure that directs or transfers fluid to the mixing area.

Figure 5:
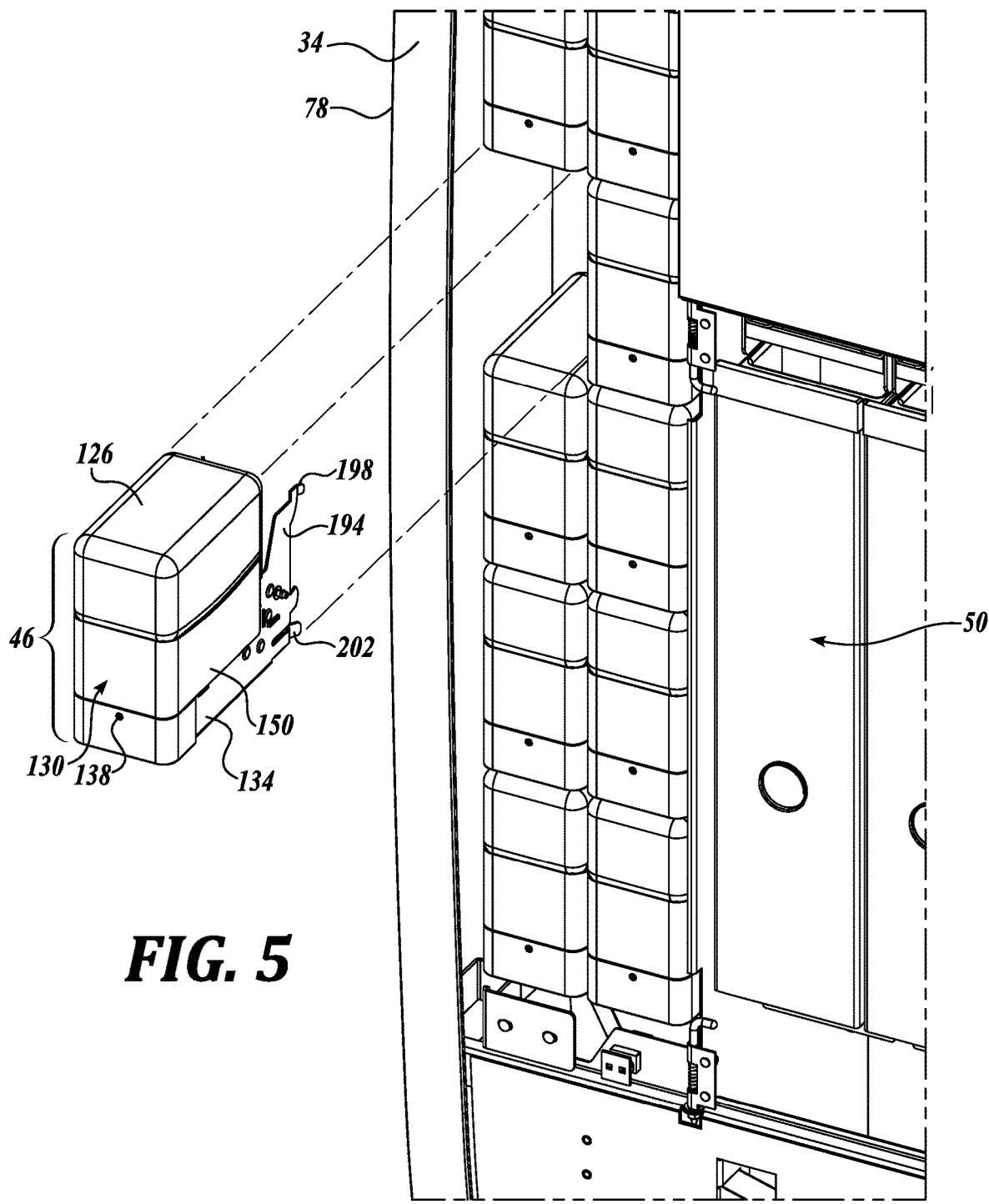
FIG. 5 is an isometric view of the dispenser of FIG. 2, showing a bead assembly exploded from the dispenser.
Figure 6:
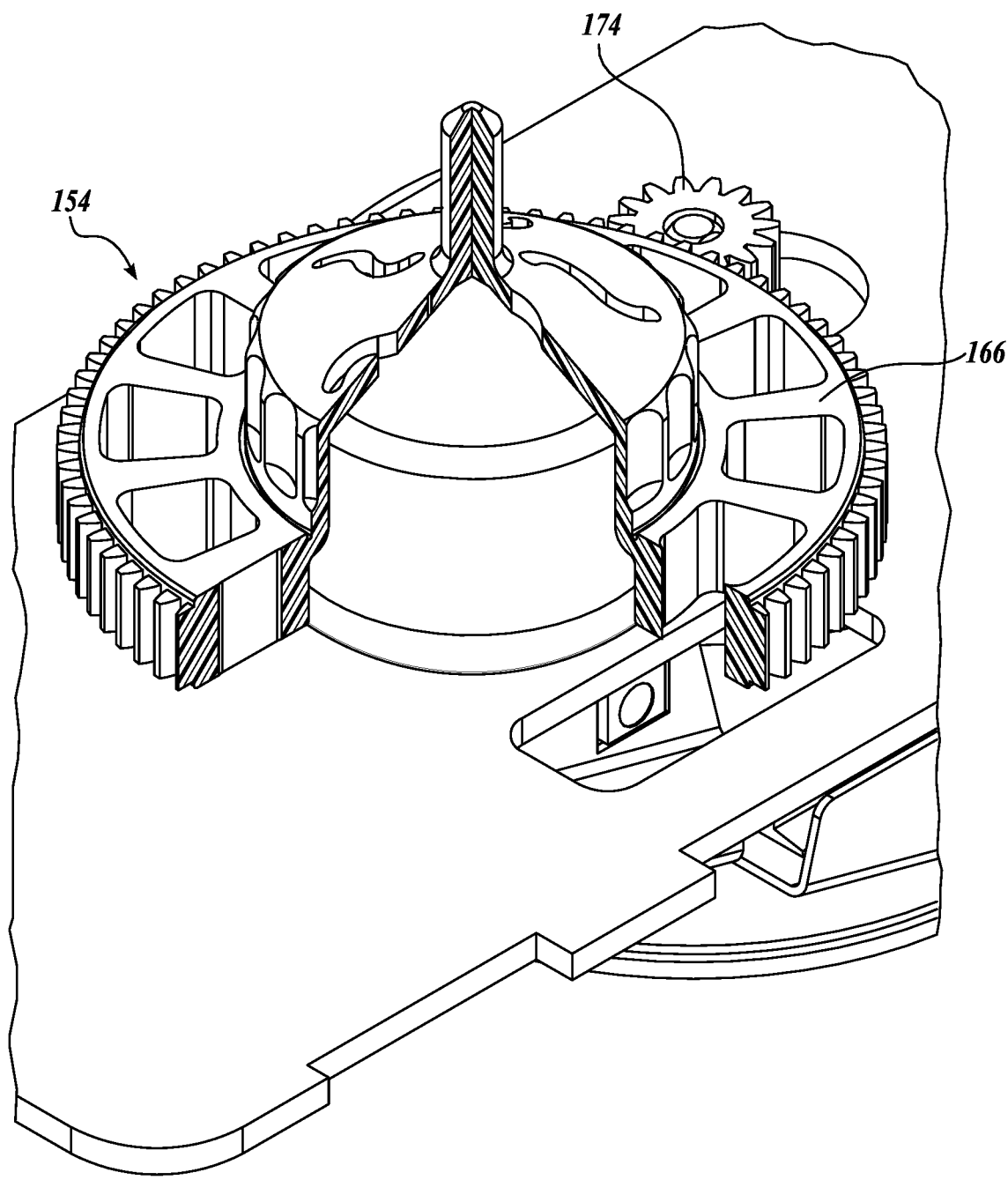
FIG. 6 is an isometric view of a portion of the bead assembly of FIG. 3.

Referring now to FIG. 5, a representative example of a bead assembly 46 is shown exploded from the dispenser 34. Each bead assembly 46 includes a bead container 126 and a singulator assembly 130 that are both supported by a subframe 134 that is configured for releasable engagement (without tools) with the main frame 114 of the dispenser 34. The bead assembly 46 has a shape that enables space-efficient vertical and horizontal stacking within the dispenser 34. In the embodiment shown, each bead assembly 46 may be loaded into the dispenser 34 from the front (where the first side 70 is located). Each bead assembly 46 may optionally include one or more visual indicators 138 (e.g., a light; level marker, etc.) that may indicate certain conditions to a user, e.g., when the bead assembly 46 needs to be replaced. Each visual indicator 138 may exhibit one or more colors and illumination patterns (e.g., flashing).

Figure 7A:
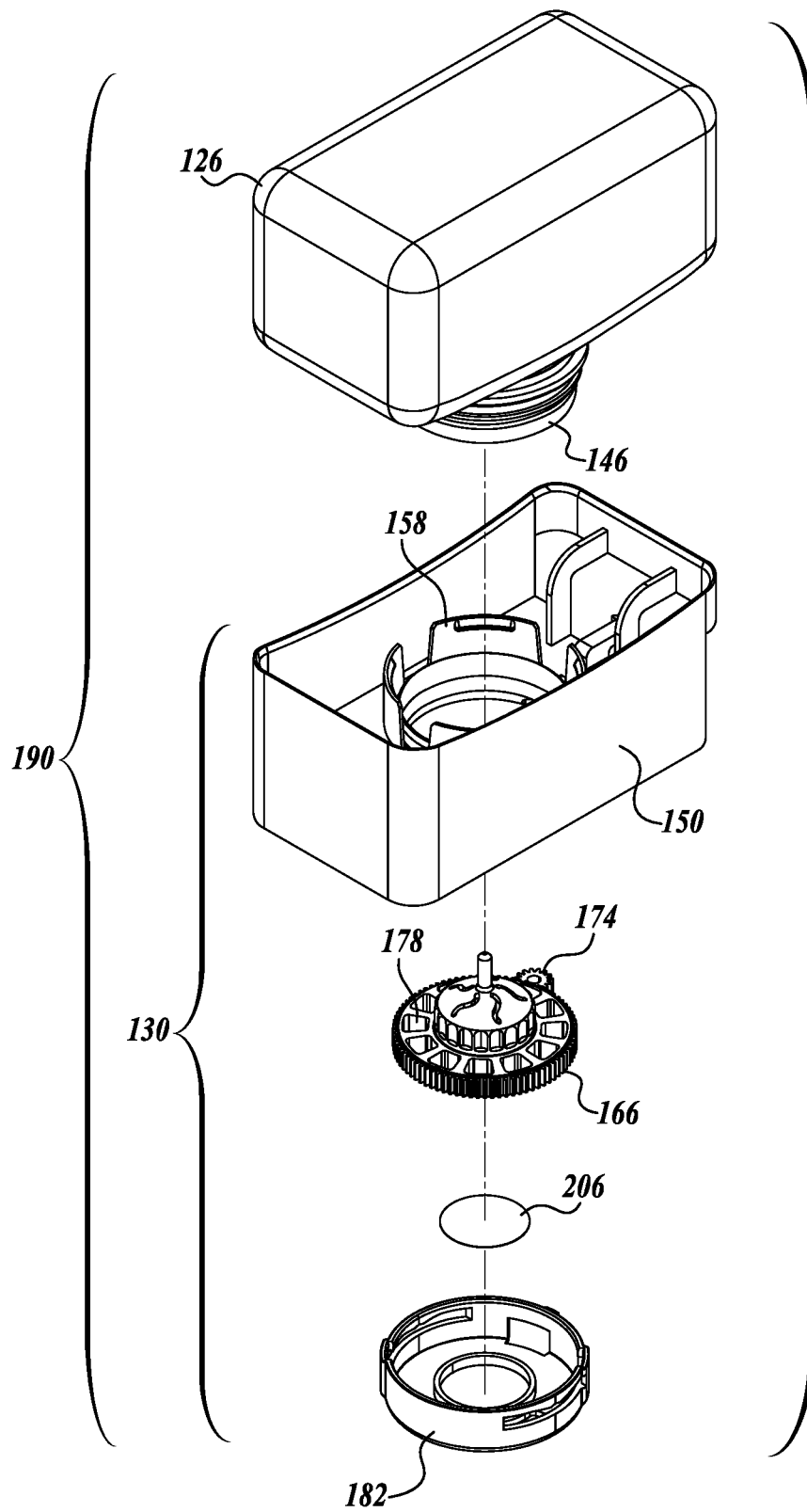
FIGS. 7A and 7B are exploded views of the bead assembly of FIG. 3.
Figure 7B:
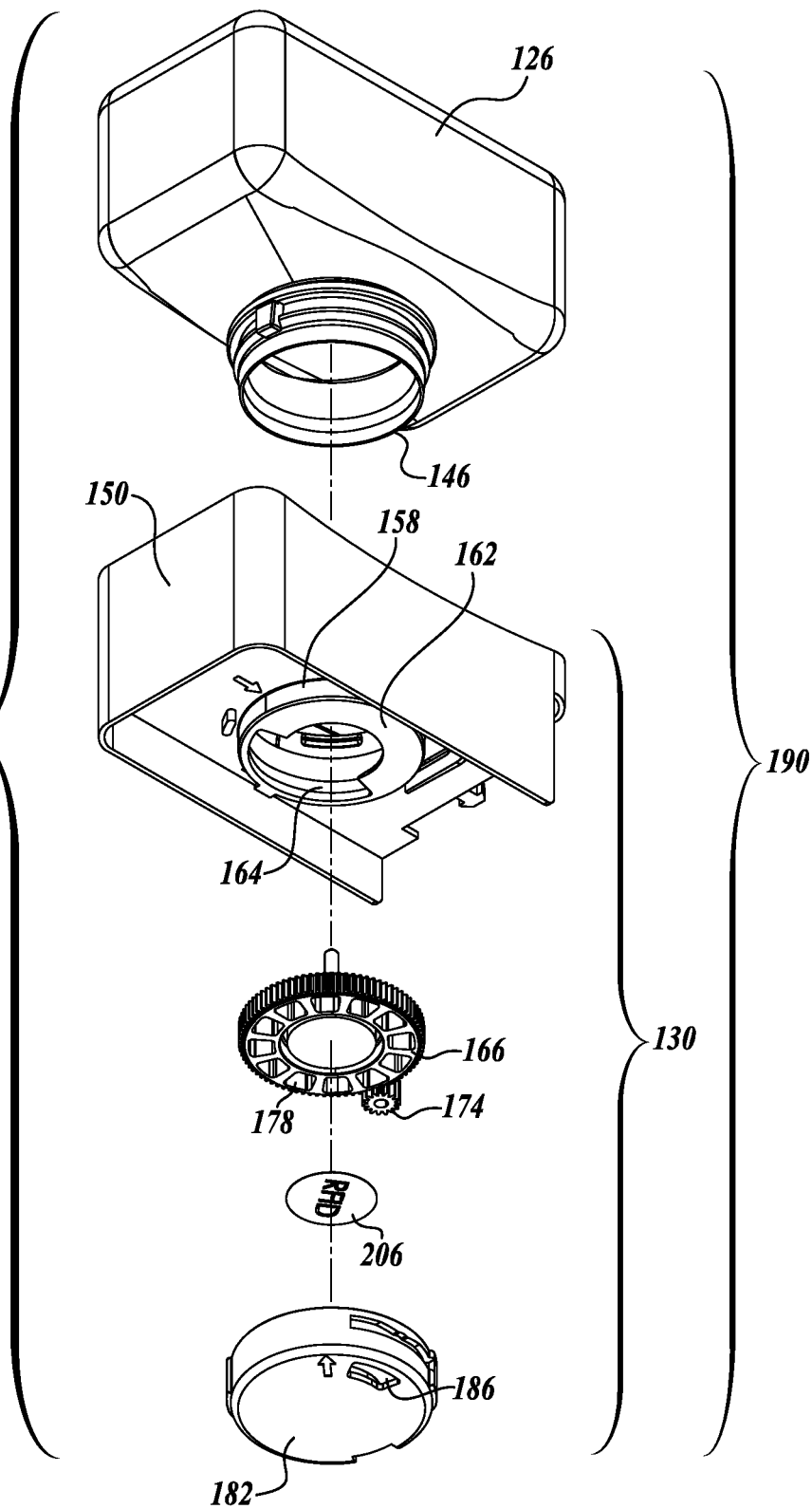
Figure 8:
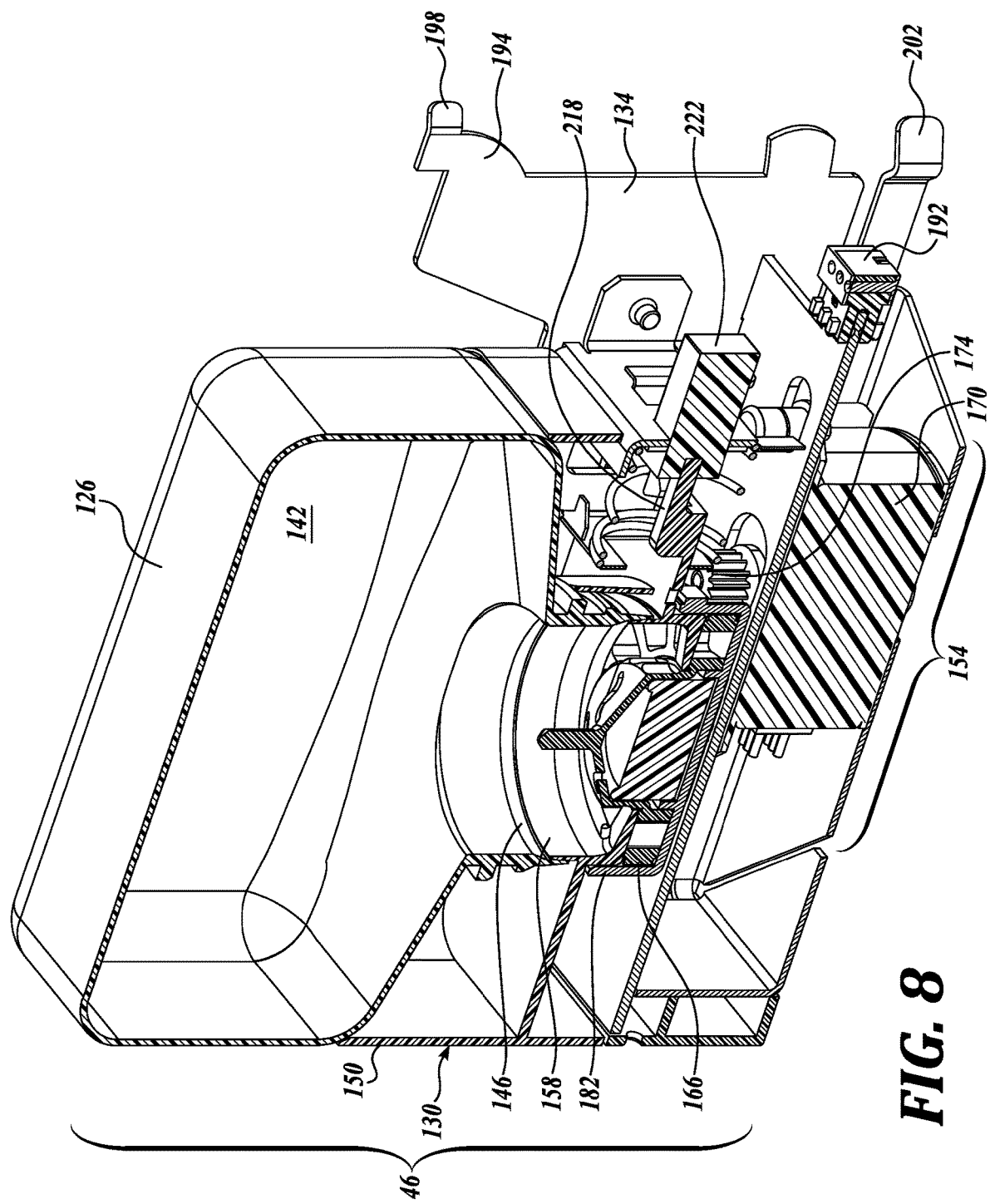
FIG. 8 is a cross-sectional view of the bead assembly of FIG. 3.

Referring to FIGS. 7A and 7B, the bead container 126 is positioned gravitationally above the singulator assembly 130 when positioned for use. In some embodiments, the bead container 126 may be made from polypropylene, polyethylene, a carbon charged plastic material to limit static electricity, or other material. As shown in FIG. 8, the bead container 126 has an internal cavity 142 that is sized to hold a quantity of beads (e.g., beads of hair dye). For example, the bead container 126 may have an internal volume of about 270 ml and hold about 2780 beads. As another example, the bead container 126 may have an internal volume of about 106 ml and hold about 500 beads. Some dispenser embodiments may include one or more bead containers having larger or smaller volumes and capacities. Some dispenser embodiments may include more than one type of bead container (e.g., one or more bead containers having a capacity of about 500 beads and one or more bead containers having a capacity of about 1,000 beads). The bead container 126 of FIGS. 7A, 7B, and 8 also has at least one mouth 146 that connects the internal cavity 142 to the singulator assembly 130 such that beads can exit the bead container 126 and enter the singulator assembly 130.

Referring to FIGS. 7A, 7B, and 8, the singulator assembly 130 includes a housing 150 that supports the bead container 126 and also contains at least some components of a singulator mechanism 154. The housing 150 includes a barrel 158 or similar structure that receives the mouth 146 of the bead container 126 and positions the bead container 126 relative to the singulator mechanism 154 (shown together in FIG. 8). The housing 150 further includes a flange 162 that extends partially around the mouth 146, leaving a flange opening 164 therethrough. In some embodiments, the barrel 158 and the bead container 126 (in particular the mouth 146) may include one or more types of retention structures such as detents, screw threads, adhesives, slots and keys, or similar structures that secure the bead container 126 to the housing 150.

Figure 9:
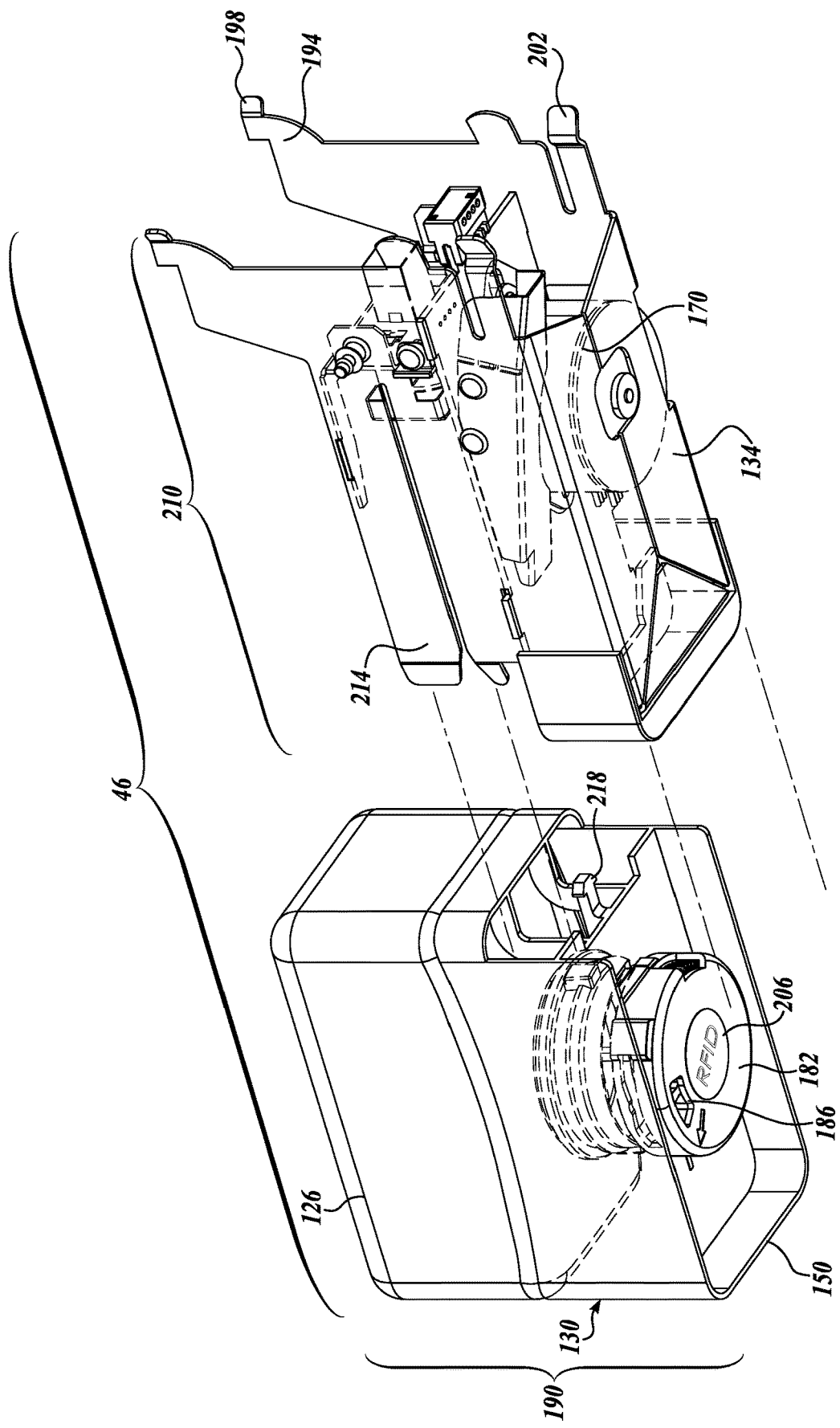
FIG. 9 is an isometric view of the bead assembly shown engaging a portion of the dispenser.

Referring still to FIGS. 7A, 7B, and 8, the singulator mechanism 154 generally includes a singulator wheel 166 that is located within the barrel 158, is gravitationally below the flange 162 of the housing 150, and is rotationally driven by a motor 170 (such as a stepper motor) via one or more gears 174 that interface with teeth of the singulator wheel 166. In some embodiments, the singulator wheel 166 may be formed from HDPE or a similar material. Similar structure, for example a belt and pulley system, could be used alternatively in some embodiments instead of gears to rotationally drive the singulator wheel 166. As shown in FIGS. 8-9, at least some components of the singulator mechanism 154 may not be located within the housing 150, but may instead by supported by and/or within the sub-frame 134. In the embodiment shown, the singulator wheel 166 is located within the housing 150 and the motor 170 is located within the sub-frame 134. The singulator wheel 166 includes an array of cavities 178 that are spaced radially away from the center and spaced about the center, each cavity 178 having a volume that is sized to receive a particular number of beads (e.g., a single bead). In operation, beads travel with the aid of gravity from the bead container 126 into the cavities 178 of the singulator wheel 166. For example, each cavity 178 may hold a single bead.

As noted above, the singulator wheel 166 is located gravitationally below the flange 162, which is located within the barrel 158 of the housing 150. A barrel cap 182 covers a bottom side of the barrel 158 (i.e., an open side) except at a barrel cap opening 186. At any given time, one or more cavities 178 of the singulator wheel 166 are located below the flange opening 164 and over the barrel cap opening 186. This way, at least one cavity 178 of the singulator wheel 166 is in communication with the space located on the opposite side of the barrel cap 182, and one or more beads may pass by the flange opening 164, through the singulator wheel 166, and through the barrel cap opening 186. When the bead assembly 46 is loaded into the dispenser 34, the barrel cap opening 186 is in communication with the primary chute 118, which carries beads from each bead assembly 46 to the mixing area 58.

When a stepper motor is used, the bead assembly 46 may dispense beads very accurately by driving the motor 170 in discrete steps. For example, the motor 170 (which is controlled by the controller 42 by suitable control signals, voltages, etc.) may rotate the singulator wheel 166 such that two cavities 178 pass over the barrel cap opening 186, thereby dispensing two (or more) beads. The motor 170 may operate at more than one speed, depending on instructions received from the controller 42. For example, if the remaining number of beads for dispensation is below a certain threshold (e.g., is fewer than 10 beads), then the motor 170 may run at a relatively low speed to ensure highly accurate dispensation. If the remaining number of beads for dispensation exceeds a threshold (e.g., is at least 10 beads), then the motor 170 may run at a relatively high speed to quickly dispense the beads.

The bead assembly 46 may optionally include one or more desiccant caps to reduce moisture. For example, a desiccant cap may be located within an opening created in the barrel cap 182 and/or the singulator wheel 166. In some embodiments, the desiccant cap may have a different location.

As described in detail below, with reference to FIGS. 5, 8, and 9, the bead container 126 and the singulator assembly 130 are supported by the sub-frame 134 that is configured for releasable engagement with the main frame 114 of the dispenser 34 without tools. As shown in FIG. 9, the bead container 126 and portions of the singulator assembly 130 (including the housing) form a replaceable and modular bead unit 190 that is removably attachable with the sub-frame 134 (e.g., is removably attachable without tools). Although the sub-frame 134 and the components contained therein are intended to be permanent, the sub-frame 134 is nevertheless removable from the dispenser 34 (e.g., without tools), such as to facilitate service, cleaning, and replacement.

As shown in FIG. 9, the sub-frame 134 includes an upper frame engagement finger 194 that extends away from the modular bead unit 190. The upper frame engagement finger 194 includes a distal prong 198, and the sub-frame 134 further includes a lower frame engagement prong 202. Both of the distal prong 198 and the lower frame engagement prong 202 are configured to releasably engage complementary apertures in the main frame 114. In the embodiment shown in FIG. 9, the sub-frame 134 includes a second upper frame engagement finger 194 and a second lower frame engagement prong 202. Together, the prongs engage the main frame 114 such that the sub-frame 134 and the modular bead unit 190 are statically supported by the main frame 114.

For example, a user may first insert the distal prong 198 at an angle into the corresponding aperture of the main frame 114, and may then rotate the sub-frame 134 until the lower frame engagement prong 202 engages the main frame 114. In such a method, the rotational movement may cause the distal prong 198 to engage the main frame 114. Some embodiments may include greater or fewer prongs, and/or may include additional or alternative forms of engagement structure other than prongs.

The modular bead unit 190 further includes a bus 192 configured to make electrical contact with a corresponding bus (not shown) of the dispenser 34 when the modular bead unit 190 is engaged with the dispenser 34. Thus, the dispenser 34 may electrically power the modular bead unit 190.

Referring to FIG. 9, the modular bead unit 190 is easily replaceable, such as when the bead container 126 exhausts its supply of beads, or when a different bead color is desired. The modular bead unit 190 may be disposable, recyclable, or reusable. In the embodiment shown, the modular bead unit 190 includes the bead container 126 and portions of the singulator assembly 130, including the housing 150, the singulator wheel 166, and the barrel cap 182. The modular bead unit 190 may include one or more devices that recognize the presence or absence of one or more conditions and communicate a signal to the controller 42 and/or the dispenser interface 38. For example, the modular bead unit 190 may include one or more optional sensors, radiofrequency identification (RFID) devices 206, and/or near field communication (NFC) devices. In such embodiments, the sensor(s) may sense one or more parameters, such as the weight of beads, the presence or absence of beads, and/or an environmental parameter within the bead container 126 (e.g., temperature).

The sensor(s) may transmit a signal to the controller 42, dispenser interface 38, and/or other components (either directly or indirectly, as through one or more intermediate components) communicating that information. For example, in an embodiment, a sensor located within the bead container 126 may sense a temperature level. When the temperature level exceeds a threshold, the sensor may send a signal to the controller 42 and/or dispenser interface 38, such as a signal to activate a climate control system. Alternatively, the sensor may send a signal indicative of ambient temperature in the bead container to the controller 42 and/or dispenser interface 38 for processing and control. As another example, a photocell located within the mouth 146 of the bead container 126 may sense the presence of beads and may additionally or alternatively count beads as they are dispensed through the mouth 146. When the photocell determines that the bead supply is exhausted, it may transmit a signal indicating this condition to the controller 42, dispenser interface 38, and/or to a visual indicator 138 on the bead assembly 46. In an embodiment, the controller 42 may determine the bead supply has fallen below a threshold. In either case, the dispenser interface 38 can then display a message (which can be a text message, an icon, or a similar message) to this effect, so that a user can remove and replace the corresponding modular bead unit 190. Similarly, the visual indicator 138 can indicate which modular bead unit 190 needs to be replaced (such as by illuminating a light or flashing a light). As another example, the RFID device 206 may transmit an identification signal corresponding to the contents of the modular bead unit 190 (e.g., corresponding to the type of bead, number of beads, date of manufacture, expiration date, etc.). The identification signal transmitted may be tracked throughout a supply chain such that each modular bead unit 190 can be traced to a series of times, locations, and potentially other identifiers. These sensor and device configurations and functions are merely exemplary.

As shown in FIG. 9, the permanent (but removable) sub-frame 134 holds certain permanent components of the singulator mechanism 154 (such as the motor 170 and the gear 174). The sub-frame 134 also forms a cradle 210 for slidably receiving the modular bead unit 190. The cradle 210 generally includes two elongate fingers 214 that each extend away from the engagement fingers 194 described above. The elongate fingers 214 may be approximately parallel to each other or may be inwardly-biased toward each other. The elongate fingers 214 and other components of the sub-frame 134 may be formed from one or more pieces of metal (e.g., steel or aluminum), plastic, or other material.

In use, the modular bead unit 190 slides into the cradle 210 as shown in FIG. 9 such that the two elongate fingers 214 engage the modular bead unit 190 and the sub-frame 134 supports the modular bead unit 190. Preferably, the elongate fingers 214 may engage the housing 150 of the singulator mechanism 154 such as by engaging one or more openings of the housing 150 (as in FIG. 9) or, in some embodiments, by grasping the outside of the housing 150. The elongate fingers 214 may engage the modular bead unit 190 more effectively if they are inwardly biased and/or include engagement structures.

The elongate fingers 214 may engage the modular bead unit 190 with additional and/or alternative structures other than the elongate fingers 214 described above. The cradle 210 and/or the modular bead unit 190 may include engagement structure separate from the elongate fingers 214 to secure the modular bead unit 190 to the sub-frame 134. For example, the modular bead unit 190 and the sub-frame 134 may include a latch system (e.g., a single-touch push-push latch system). In some embodiments, the modular bead unit 190 may include some components of the latch system, and the sub-frame 134 may include complementary components.

In FIG. 9, the modular bead unit 190 includes an engagement member 218, and the sub-frame 134 includes a receiver 222 that is positioned to receive the engagement member 218 when the modular bead unit 190 is placed within the cradle 210. When the modular bead unit 190 is positioned in the cradle 210, the user may apply a single force (e.g., a single pushing force) to cause the elongate fingers 214 of the sub-frame 134 to engage the housing 150 of the modular bead unit 190, and to cause the receiver 222 to receive the engagement member 218 that projects away from the modular bead unit 190. At this time, the sub-frame 134 securely holds the modular bead unit 190 in the cradle 210. A reader located on the dispenser 34 may interpret data broadcast by the RFID device/NFC of the modular bead unit 190 (e.g., to confirm that the correct modular bead assembly 190 has been installed). When it is time to replace the modular bead unit 190, a user may apply a single force (e.g., a single pushing force) to a rear side of the modular bead unit 190 to cause the receiver 222 to release the engagement member 218, at which time the user may replace the modular bead unit 190.

Figure 10:
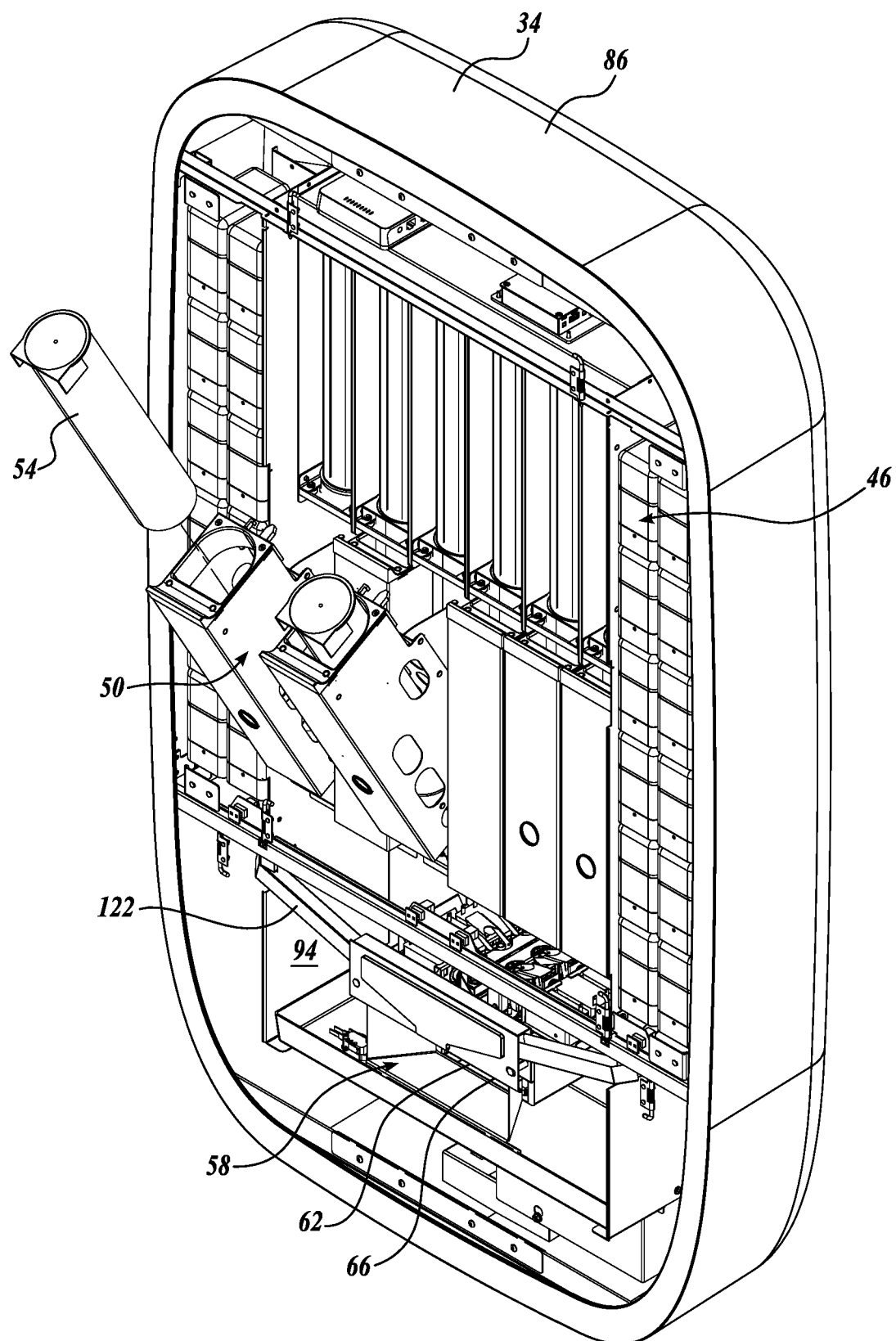
FIG. 10 is an isometric view of the dispenser of FIG. 2, showing one representative embodiment of a cartridge exploded from the dispenser.

As noted above and with reference to FIG. 10, the dispenser 34 includes a plurality of cartridge assemblies 50, each of which generally stores one or more cartridges 54 of a fluid, e.g., a developer, a formulation, a liquid, a lotion, a cream, a diluter, etc. In some embodiments, such fluids may be stored in different forms other than cartridge assemblies. The non-limiting embodiment shown in FIG. 10 includes six exemplary cartridge assemblies 50, each of which is movable between a closed state and an open state. In FIG. 10, four cartridge assemblies 50 are shown in the closed state and two are shown in the open state. In the closed state, the cartridge 54 is positioned to dispense the stored fluid. In the open state, the cartridge 54 may be removed and replaced with a similar cartridge 54; in this way, the cartridges 54 are modular.

The representative cartridge assembly 50 shown in FIGS. 11A and 11B includes the cartridge 54, which is received within a carriage 226. The carriage 226 is selectively movable between a closed state (FIG. 11A) and an open state (FIG. 11B). Each cartridge assembly 50 may optionally include at least one visual indicator 230 (e.g., a light, level marker, etc.) that may indicate certain conditions to a user, e.g., when the cartridge 54 needs to be replaced. Each visual indicator 230 may exhibit one or more colors and illumination patterns (e.g., flashing). The visual indicator(s) 230 may be operatively connected to the controller 42 and/or to one or more sensors. For example, when a sensor senses when the cartridge 54 is exhausted, or when a fluid level falls below a threshold, the controller 42 may cause the visual indicator 230 to illuminate.

The cartridge 54 may have a variety of forms and may be manufactured from a variety of materials. As one non-limiting example, the cartridge 54 may have an internal volume of about 500 mL to about 1.5 L (e.g., about 1 L) and may be manufactured from HDPE or similar material, such as dosing cartridge reference number 24011-0001, manufactured by Ritter Cartridges. The cartridge 54 may be disposable, recyclable, or reusable. Similar to the modular bead unit 190, each cartridge 54 and/or cartridge assembly 50 (including any cartridge and pouch assembly described in this application) may include one or more sensors, radiofrequency identification (RFID) devices, and/or near field communication (NFC) devices. In such embodiments, the sensor(s) may sense one or more parameters, such as the weight of fluid within the cartridge 54, the presence or absence of fluid in the cartridge 54, and/or other property of the fluid stored within the cartridge 54. The sensor(s) may communicate information by transmit a signal to the controller 42 and/or the dispenser interface 38 (either directly or indirectly, as through one or more intermediate components). Additionally or alternatively, the RFID device may transmit an identification signal corresponding to the contents of the cartridge 54 (e.g., corresponding to the type of fluid, date of manufacture, expiration date, etc.). The identification signal transmitted by the RFID device may be tracked throughout a supply chain such that each cartridge 54 can be traced to a series of times and locations. These sensor and RFID configurations and functions are merely representative.

As shown in FIG. 11B, the carriage 226 includes an internal space 234 that is sized to receive the cartridge 54. The internal space 234 may be at least partially complementary to the shape of the cartridge 54, but may be sized to receive more than one cartridge size. The carriage 226 may include one or more hinges or similar structure to enable movement between the open and closed states. When the carriage 226 is in the open state shown in FIG. 11B, a user may load the cartridge 54 by inserting it into the internal space 234. The cartridge 54 and the carriage 226 may include complementary retention structure such as a single-touch mechanism (e.g., a push-push mechanism) to retain the cartridge 54 within the carriage 226 until it needs to be replaced.

In the closed state shown in FIG. 11A, a first end 238 (an upper end) of the carriage 226 and a first end 242 (an upper end) of the cartridge 54 interface with a drive assembly 246. In the non-limiting embodiment of FIGS. 11A and 11B, the drive assembly 246 includes a motor (e.g., a stepper motor) that is operatively connected to a lead screw, which is connected to a piston (such as an LDPE piston). In use, the controller 42 drives the motor, and the motor drives the piston toward the first end 242 of the cartridge 54 to dispense fluid from a second end 250 of the cartridge 54 (a lower end). When a stepper motor is used, the cartridge assembly 50 may dispense fluid very accurately (e.g., to within about 0.1 mg of a target weight) by driving the motor by a number of discrete steps. This accurate dispensing is possible even without utilizing a load cell in the mixing area 58 to confirm the dispensed weight.

Figure 12:
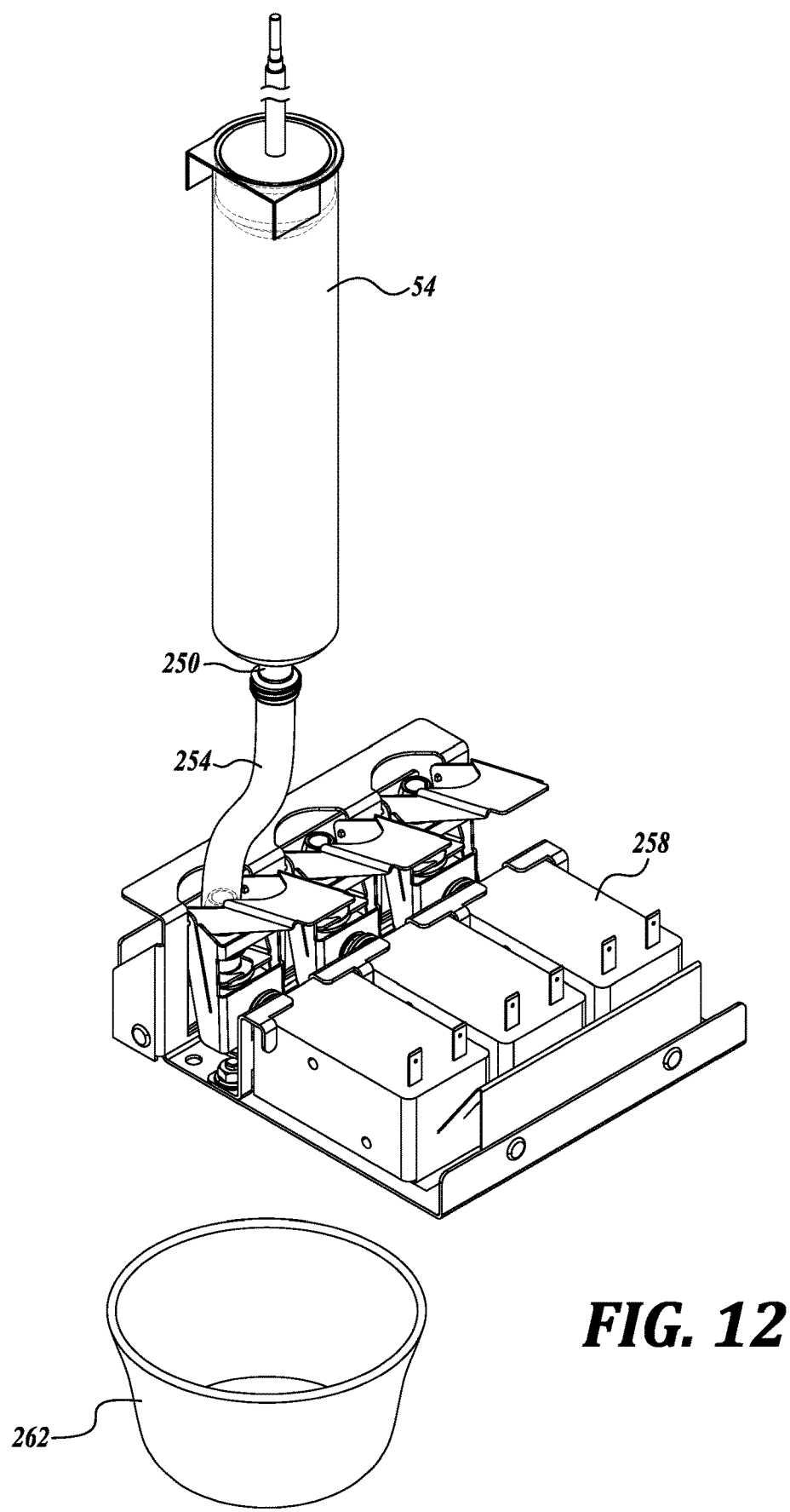
FIG. 12 is an isometric view of the cartridge of FIG. 10 shown exploded from the dispenser of FIG. 2, wherein the cartridge is shown in operable connection with a portion of the dispenser.

FIG. 12 shows the cartridge 54 independently of the carriage 226 and the drive assembly 246. As shown, the second end 250 of the cartridge 54 may be connected to a tube 254. An end of the tube 254 may connect to a duckbill valve or other similar structure to improve precision, accuracy, and cleanliness, e.g., by reducing or eliminating a "tail." The tube 254 may pass through a solenoid valve 258 (e.g., a linear solenoid valve), which may further improve dispensing precision and accuracy by quickly opening and closing the tube 254 by pushing against the tube 254. In any of the embodiments described herein (including cartridge embodiments and pouch embodiments described below), the tube 254 may be replaced (e.g., at the same time the cartridge 54 is replaced) in order to eliminate cleaning steps, to minimize microfluidic footprint, to prevent cross-contamination, or for other advantages. The cartridge 54 may be located gravitationally above a vessel 262 (e.g., a bowl), such that fluid may dispensed from the cartridge 54 into the vessel 262. The vessel 262 is representative of vessels that may be utilized in any embodiment disclosed herein. Some embodiments may include a sensor, such as a load cell, positioned beneath or above the vessel 262 to sense the weight of the dispensed fluid(s). Accordingly, the load cell may be operatively connected with the controller 42 and/or the dispenser interface 38.

Referring again to FIGS. 11A and 11B, although the carriage 226 and the drive assembly 246 are intended to be permanent, those elements may nevertheless be removable from the dispenser 34, such as to facilitate service, cleaning, and replacement. The carriage 226 and the drive assembly 246 may interface with the main frame 114 (as shown in FIG. 3) in a similar manner as the bead assembly 46. For example, the non-limiting drive assembly 246 shown in FIGS. 11A and 11B includes a plurality of engagement members 266 (e.g., prongs) that are configured to engage complementary apertures the main frame 114 of the dispenser 34, such that the main frame 114 supports the carriage 226 and drive assembly 246.

Referring again to FIG. 2, the dispenser 34 may optionally include a climate control system 270, such as may be configured to regulate the temperature and/or humidity within the dispenser 34. The climate control system 270 may prolong the life of one or more products contained within the dispenser. For example, the climate control system 270 may prolong the life of beads contained within the bead assemblies 46, as some beads are moisture-sensitive. The climate control system 270 may be operatively connected to the controller 42 and/or the dispenser interface 38. In the non-limiting embodiment of FIG. 2, the climate control system 270 is a Peltier-type system that creates temperature gradients utilizing electric current, although other types of climate control systems are contemplated. In an embodiment, the climate control system 270 may include or be augmented by a desiccant in order to regulate humidity in the dispenser 34. In such a configuration, the climate control system 270 may be a peltier-type system that is augmented by a desiccant. In such a configuration, the desiccant passively regulates the humidity within the dispenser 94, and the peltier-type climate control system 270 actively may be configured to operate in response to a trigger (e.g., door open or a humidity surge); thus, the desiccant and peltier system provide complementary functionality. In an embodiment, the climate control system 270 may include a desiccant without a peltier system, and therefore may be entirely passive.

The climate control system 270 may be positioned adjacent the fourth side 82 (the right side) and the sixth side 90 (the bottom side) in the embodiment of FIG. 2, but may have different positions in other embodiments. In some embodiments, the climate control system 270 may include one or more sensors (e.g., a humidity sensor located within the dispenser). In some embodiments, the climate control system 270 may be electrically connected to the controller 42 and/or the dispenser interface 38, which may also be electrically connected to one or more sensors. When a sensor (e.g., a humidity sensor) senses that a condition within the internal space 94 of the dispenser 34 deviates from a certain value (e.g., when actual humidity exceeds or falls below a humidity threshold), then the sensor may transmit a signal to the controller 42, which may then transmit a signal to the climate control system 270 (e.g., to turn the climate control system 270 on or off). In some embodiments, the climate control system 270 may not be connected to the controller 42.

Figure 13:
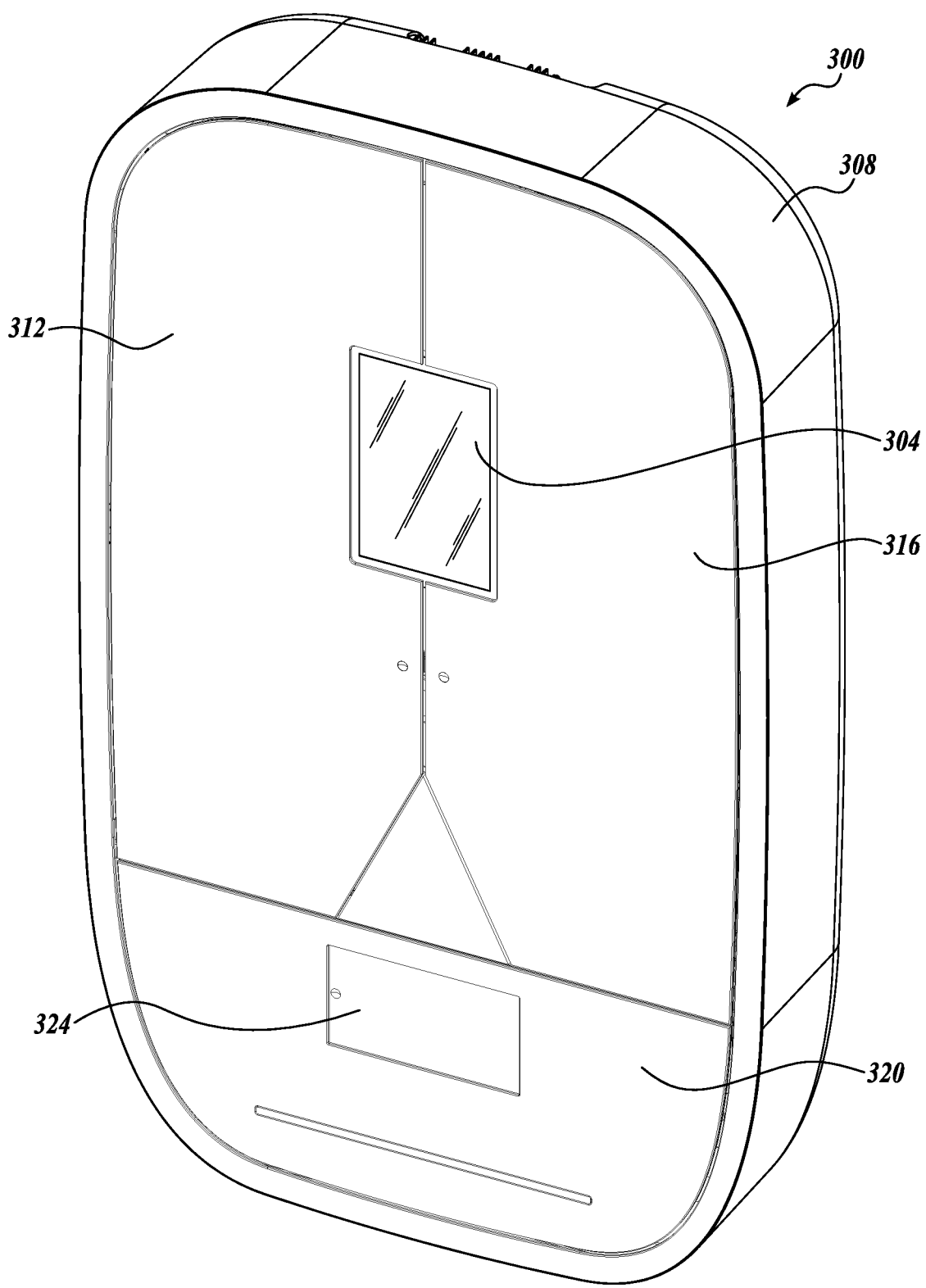
FIG. 13 is an isometric view of aspect of a custom formulation system formed in accordance with another representative embodiment of the present disclosure.

FIGS. 13-16 show another representative custom formulation system 300, which includes many similar elements as the embodiment of FIGS. 1-12, including a user interface 304 and a dispenser 308. The embodiment of FIG. 13 is non-limiting; the specific structures and functionalities of FIG. 13 are not limited to the illustrated embodiment, and may be practiced in whole or in part in other embodiments. The structural and functional features of the embodiment of FIG. 13 may be combined with functional and structural features of other embodiments (e.g., the embodiment of FIG. 11), and vice versa. The dispenser 308 includes a first panel 312 (a left panel), a second panel 316 (a right panel), and a third panel 320 (a lower panel). The user interface 304 is integrated with the dispenser 308 in between the first panel 312 and the second panel 316. The third panel 320 includes a door 324 that conceals a mixing area 328 (which may include a platform or other bowl supporting system), the door 324 and the mixing area 328 being sized to receive a mixing vessel 332 (e.g., a cup).

Figure 14:
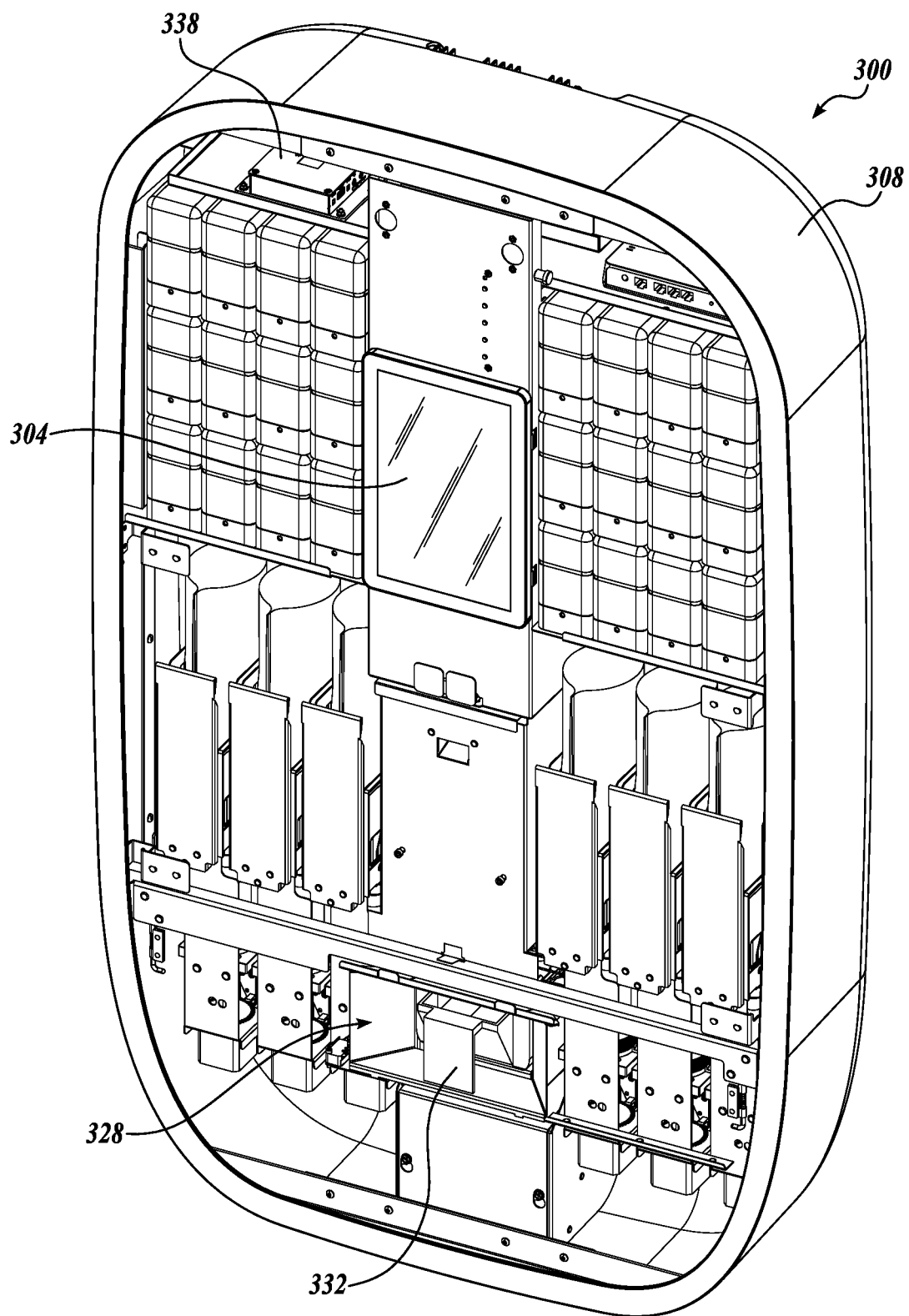
FIG. 14 is an isometric view of the dispenser of the custom formulation system of FIG. 13, with a portion of the dispenser hidden to view the internal components.

FIG. 14 shows the dispenser 308 of FIG. 13 with the first panel 312, the second panel 316, and the third panel 320 removed to show an internal space 336 of the dispenser 308. The dispenser 308 contains a controller 338, a number of bead assemblies 340 (e.g., twenty-four) and a number of fluid formulation assemblies—in this embodiment, pouch assemblies 344 (e.g., six). When the dispenser 308 is positioned for operation, the bead assemblies 340 and the pouch assemblies 344 are located gravitationally above the mixing area 328. The bead assemblies 340 are configured in arrays having vertically-organized and horizontally-organized aspects, while the pouch assemblies 344 are arranged in a horizontally-organized array. Each bead assembly 340 is constructed in a similar manner as the bead assembly 46 shown in FIGS. 5-9.

Figure 15:
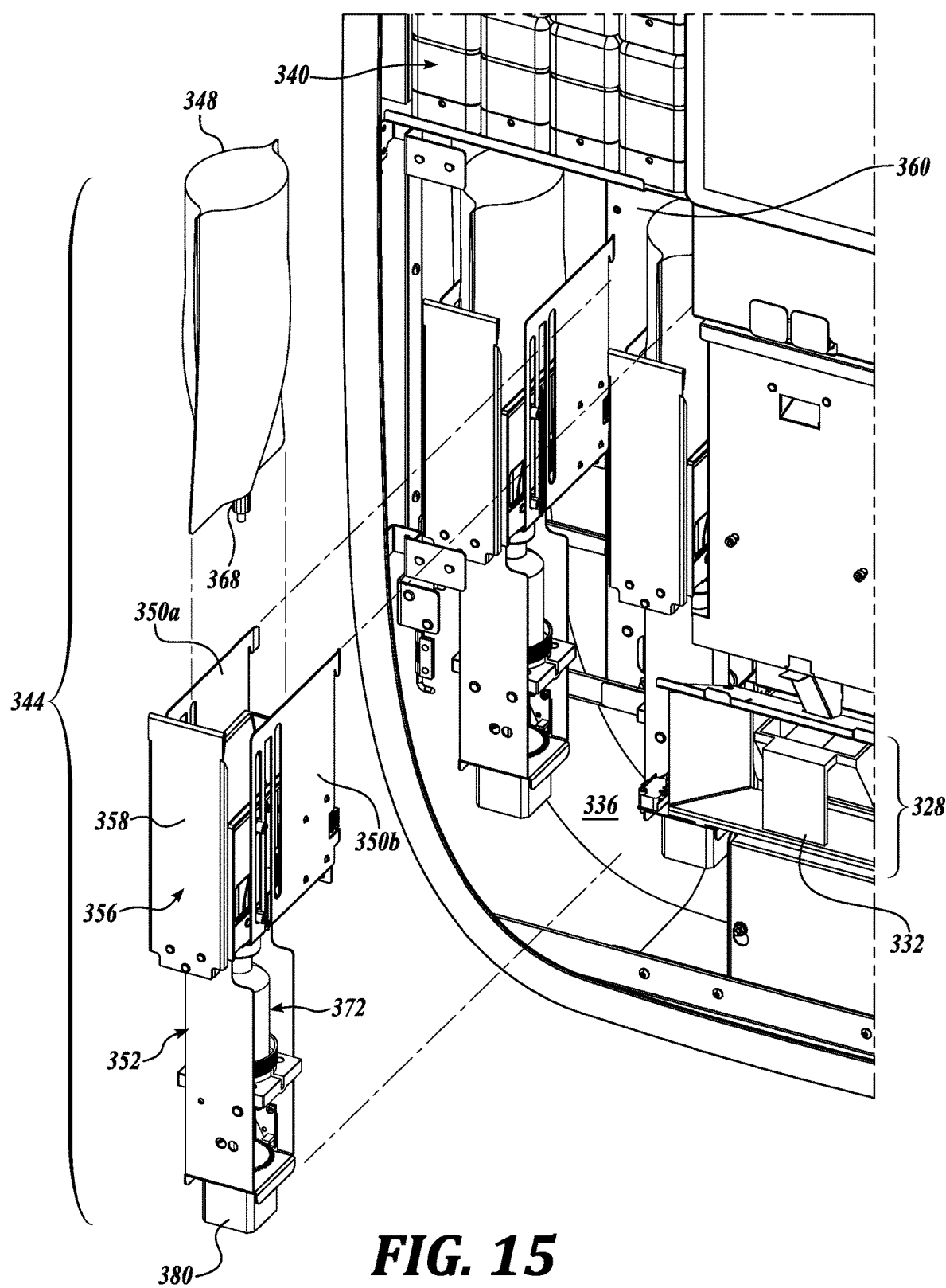
FIG. 15 is an isometric view of the dispenser of FIG. 13, showing one representative embodiment of a pouch assembly exploded from the dispenser.
Figure 16:
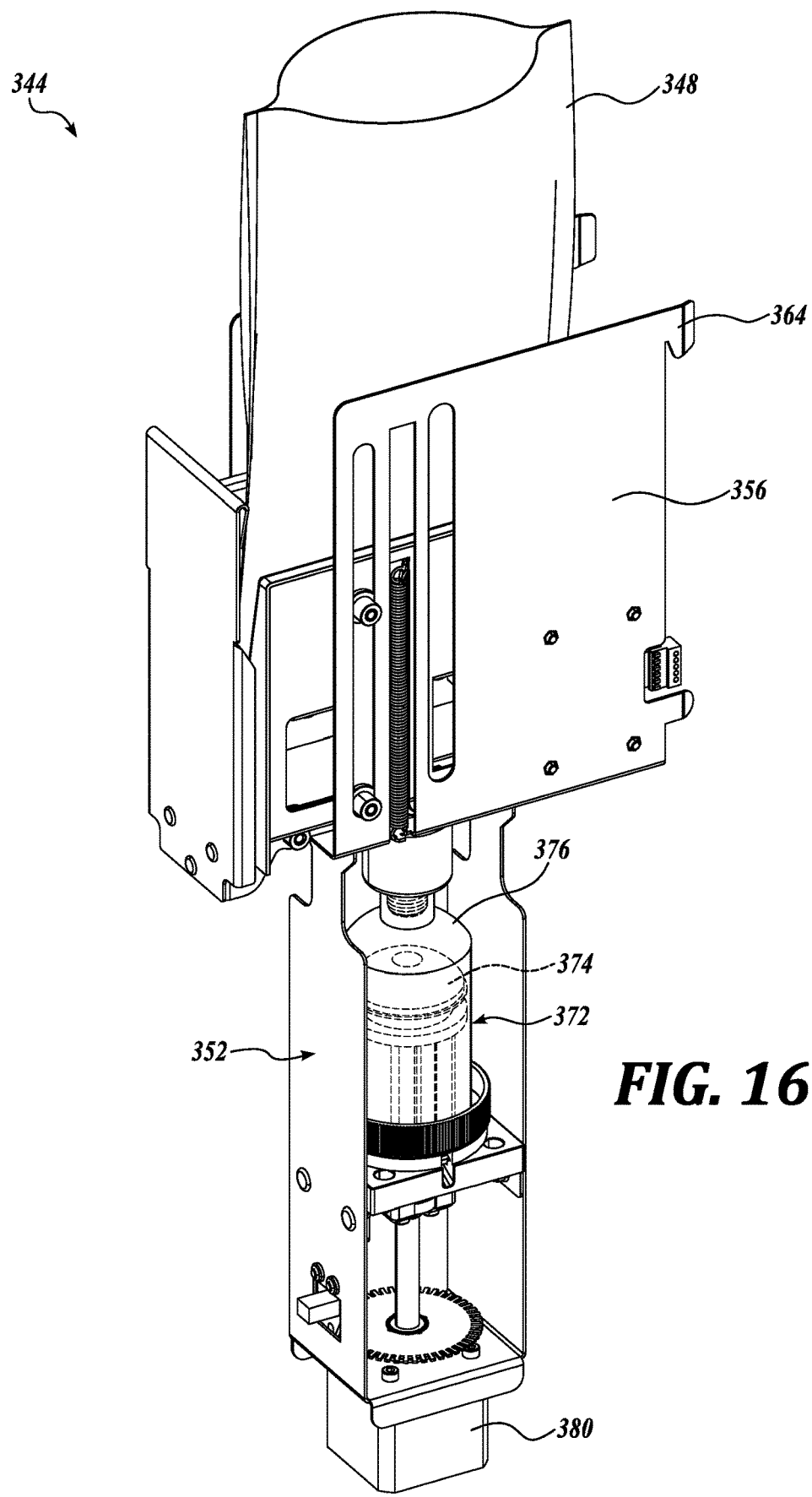
FIG. 16 is an isometric view of the pouch assembly of FIG. 15.

FIGS. 15 and 16 show one pouch assembly 344 exploded from the dispenser 308. The pouch assembly 344 is designed to store and dispense fluids, e.g., developers, formulations, fluids, lotions, creams, diluters, etc. The pouch assembly 344 includes a pouch 348 and a pump sub-assembly 352 that is in fluid communication with the contents of the pouch 348. The pouch 348 is designed to be easily and inexpensively replaceable, whereas the pump sub-assembly 352 is designed to be permanent. A carriage 356 supports the pouch 348, two paddles 350a and 350b, and the pump sub-assembly 352, and may be removably attachable with a main frame 360 of the dispenser 308 in a similar manner as the carriage 226 of the cartridge assembly 50 described above, e.g., with one or more engagement members 364 (e.g., prongs) and/or similar engagement structures.

The pouch 348 may have a volume of about 500 mL to about 1500 mL, and may be formed from one or more layers, such as a laminate structure. One or more of the layers may include polypropylene or other material for corrosion protection. One or more of the layers may provide photosensitive protection to the fluid within the pouch 348. The pouch 348 has a pouch outlet 368 (which may include a fitment) that is removably attachable with the pump sub-assembly 352. The pouch outlet 368 may act as a check valve, for example to prevent leakage or oxidation of the fluid contents and/or to ensure proper operation with the pump sub-assembly 352.

To remove the pouch 348 from the carriage 356, a user can pull down on a handle 358, and slide the pouch 348 out from between the paddles 350a and 350b toward the handle 358. The reverse process can be utilized to insert the pouch 348 into the carriage 356. When the handle 358 is closed, it engages the pouch fitment 359 with the pump sub-assembly 352.

In an embodiment, the pump sub-assembly 352 includes a three-way fluidic connection having three sides connected by a junction. The pouch 348 connects to a first end of the three-way fluidic connection (an upstream end) by a first check valve (e.g., an umbrella valve or pinch valve). A second check valve (e.g., a duckbill valve, or pinch valve) is located near a second end (a downstream end) of the three-way fluidic connection, and a pump 372 is in fluid communication with a third end of the three-way fluidic connection. Other embodiments may have additional or fewer fluidic connections (e.g., a two-way or four-way fluidic connection).

The pump 372 may be a syringe-type pump that includes a piston 374 that moves within a chamber 376 to create negative and positive pressure within the chamber and the T-connection. The chamber 376 may have a volume of about 10 mL to about 100 mL, e.g., about 40 mL. To precisely move the piston 374, the pump 372 may include a motor 380 (e.g., a stepper motor) that drives a lead screw connected to the piston 374. The controller 338 drives the motor 380.

In operation, the pump 372 may draw fluid from the pouch 348 and into the chamber 376 by moving the piston 374 away from the pouch 348 (e.g., by rotating the motor 380 by a predetermined amount that corresponds with the volume of fluid to be drawn). When the predetermined amount of fluid is drawn from the pouch 348 and into the chamber 376, the pump 372 reverses the piston 374 to drive the fluid out of the chamber 376 and clean cut the tail of fluid flow. Due to the presence of the first check valve or pinch valve (which may be the pouch outlet 368), the fluid cannot reenter the pouch 3448 and is directed through the second check valve or pinch valve and the second end of the T-connection and ultimately into the mixing area 328. The In some embodiments, the dispenser 308 may include an alternative pouch assembly instead of, or in addition to, the pouch assembly 344 described above. The alternative pouch assembly may include a pouch 348 as described above, in fluid connection with a peristaltic pump. Such an embodiment may have a single fluid channel connecting the pouch 348 to the mixing area 328 (rather than a T-connection). In such an embodiment, the peristaltic pump would be positioned in-line with the fluid channel between the pouch 348 and the mixing area 328 such that the peristaltic pump would draw fluid from the pouch 348 and through a pump inlet, and then dispense fluid out of a pump outlet to the mixing area 328.

Figure 17:
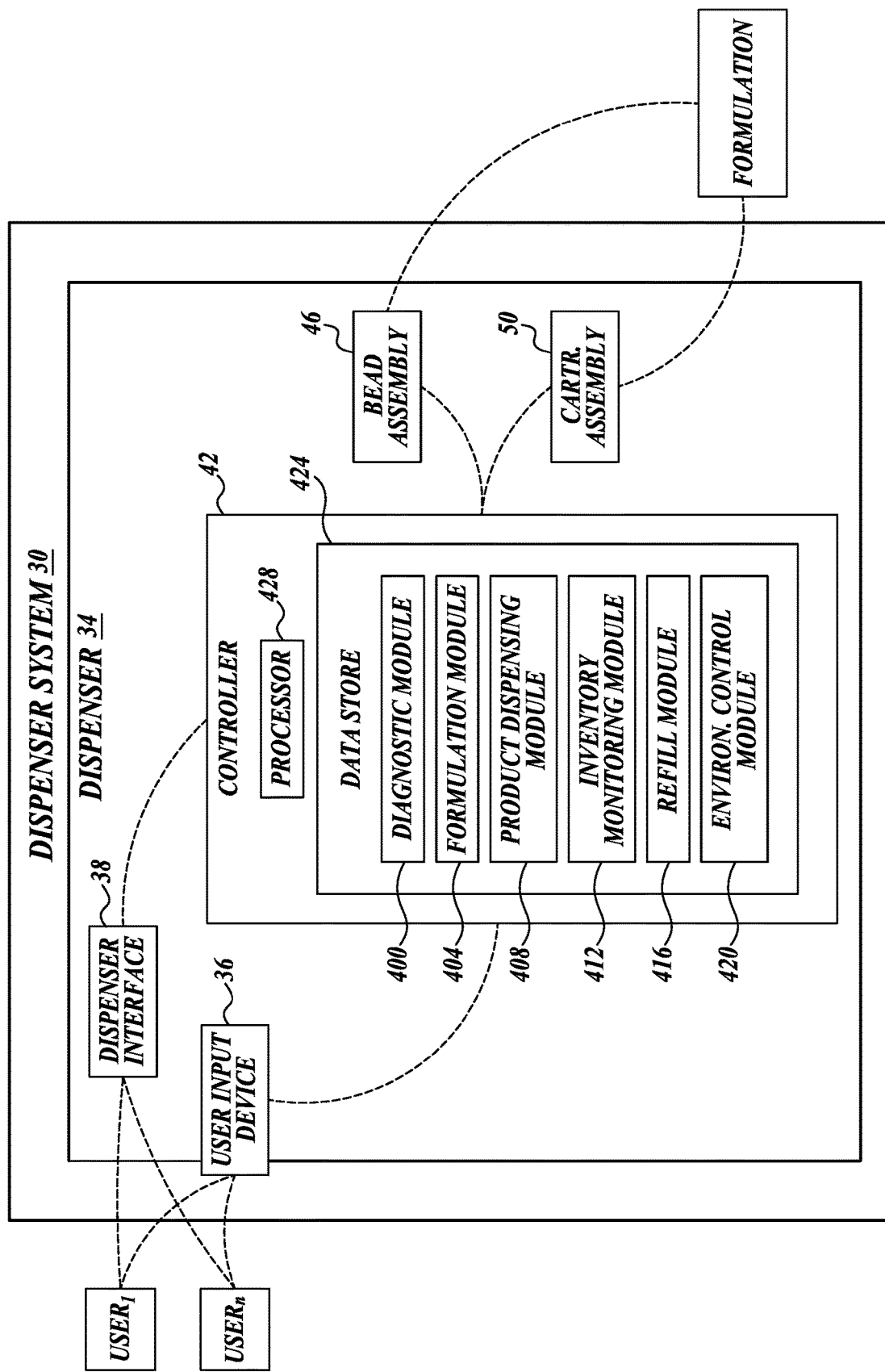
FIG. 17 is a functional block diagram illustrating components of a custom formulation system, in accordance with an embodiment of the disclosure.

Referring now to FIG. 17, the formulation system 30 stores one or more modules that may be implemented as software logic (e.g., executable software code), firmware logic, hardware logic, or various combinations thereof. Any of the following modules or combinations thereof may be implemented as a computer program product stored on a non-transitory computer-readable medium that includes instructions that, when loaded into memory, cause a processor to perform one or more methods set forth herein.

Exemplary modules include: a diagnostic module 400, a formulation module 404, a product dispensing module 408, an inventory monitoring module 412, a refill module 416, and an environmental control module 420. These modules are exemplary and non-limiting. In an embodiment, the custom formulation system contains additional modules. In an embodiment, the custom formulation system includes fewer modules. In an embodiment, steps described below with respect to any single module may be contained in more than one module, and steps described below with respect to more than one module may be contained in a single module.

The logic, algorithms, interactions, effects, relationships, properties, and other factors utilized by the modules of FIG. 17 are stored on the data store 424. In an embodiment, any module may be stored in part or in whole on external storage resources and/or on one or more components of the formulation system 30 having a data store, including the user input device 36, dispenser interface 38, controller 42, any other component of the formulation system 30 having a data store, and/or external storage resources (e.g., cloud-based processing and storage systems such as AMAZON WEB SERVICES®). Likewise, the modules of FIG. 17 are associated with a processor 428 of the controller 42; however, any module may be executed in part or in whole on one or more components of the formulation system 30 having a processor, including the user input device 36, dispenser interface 38, controller 42, any other component of the formulation system 30 having a processor, and/or external computing resources. Similarly, any module may be initiated automatically (such as through another module), by the user input device 36, dispenser interface 38, or other component (which may be configured to receive user inputs). Generally, any input that is described below as being input into the user input device 36 may—in another embodiment or in the same embodiment—be input into the dispenser interface 38, and vice versa. Likewise, any input that is described below as being input by a customer may alternatively be input by a stylist or technician. Any module may cause the user input device 36 and/or the dispenser interface 38 to display one or more visual representations (e.g., a specific graphical user interface). For example, any module may cause the user input device 36 and/or dispenser interface 38 to display a graphical user interface ("GUI") that is configured to receive inputs from one or more actors, including a customer, a hair stylist, a technician, and/or other actors. For example, any module may create a customer-facing GUI that limits the number of potential inputs to simplify use. Similarly, any module may create a stylist GUI, a technician GUI, and/or additional GUIs for specific purposes.

The diagnostic module 400 diagnoses a user's initial hair state and a target hair state. A user (e.g., a customer and/or a stylist) provides one or more inputs into the user input device 36 corresponding to a present hair state of the customer (e.g., color, texture, thickness, nationality, age, damage, environmental conditions, straight, curly, treated, gray, inputs from remote devices, etc.). The user also provides one or more inputs into the user input device 36 corresponding to a target hair state (e.g., color, straight, curly, etc.). To assist the user, the user input device 36 and/or the dispenser interface 38 may display a menu of present hair state options (including a present hair state representation) and target hair state options (including a target hair state representation, which may be based upon an image provided by the customer). Based upon the inputs corresponding to the present and target hair states, the diagnostic module 400 creates a first and a second input sets, respectively. The user input device 36 and/or the dispenser interface 38 may display one or more images, illustrations, messages, and/or other visual or graphical representations corresponding to any of the inputs (e.g., an image corresponding to the target hair condition, including a predicted hair color), and/or to validate any user input. In an embodiment, the user input device 36 and/or the dispenser interface 38 may communicate with a digital assist platform including GOOGLE ASSISTANT®, AMAZON ALEXA®, or other digital assist platform to facilitate selection of inputs corresponding to the present hair condition and/or target hair condition. For example, in an embodiment, the user may query the digital assist platform to search for images of the target hair condition. In an embodiment, the user may query the digital assist platform to determine whether the target hair state will be fashionable.

After the user provides the inputs corresponding to the present and target hair conditions, the diagnostic module 400 diagnoses the customer's present hair condition, such as by analyzing the first and second input sets (e.g., to determine compatibility with certain formulations), classifying the customer's hair (e.g., by color, texture, etc.), and by generating a summary of inputs (corresponding to the initial and/or target hair states) for display on the user input device 36. In an embodiment, the diagnosis module 400 may classify or diagnose a hair condition based upon the inputs corresponding to the customer's initial hair state, and based upon known relationships between the inputs and hair conditions. For example, it may diagnose the customer's hair as damaged if the present hair condition includes dryness, split ends, or dull color, etc. In an embodiment, the stylist may provide one or more inputs to influence the diagnosis by the formulation system 30. In an embodiment, the stylist may separately diagnose a hair condition.

The formulation module 404 computes a formulation recipe that is formulated to change the customer's hair condition from the present hair condition to the target hair condition. The formulation module 404 computes the formulation recipe by analyzing the first and second input sets (corresponding to the customer's present hair state and target hair state, respectively), and then selecting one or more formulation ingredients (e.g., at least one dye, lotion, cream, diluter, etc.) that, when applied to the customer's hair, are expected to change the customer's hair to achieve the target state. The formulation module 404 may select a plurality of formulations for the formulation recipe by considering, for example: known interactions between formulations (such as when the plurality is mixed); known effects of particular formulations on particular hair types and conditions; formulation chemical properties; and other factors and relationships.

The formulation recipe may include one or more dyes (e.g., about 1 dye to about 30 dyes, e.g., 4 dyes, 5 dyes, and 6 dyes), each dye having a volume (and/or a number of beads that correspond to a volume). The number of potential dyes in the formulation recipe may be limited by the number of bead assemblies 46 installed in the dispenser 34. The formulation recipe may additionally or alternatively include one or more fluids such as developers, lotions, creams, diluters, etc. (e.g., about 1 fluid to about 10 fluids, e.g., 2 fluids, 3 fluids, 4 fluids, 5 fluids, and 6 fluids), each fluid having a volume. The number of potential fluids in the formulation may be limited by the number of cartridge assemblies 50, pouch assemblies 344, and other such assemblies installed in the dispenser 34. The formulation recipe may specify the order in which particular ingredients are to be dispensed, intermediate steps (including manual mixing by a user), and the timing for any step (including delays between steps, such as to give beads time to disintegrate). In some formulation recipes, the number of fluids may vary, the volume dispensed of each fluid may vary, the number of bead types may vary, the quantity of each bead type dispensed may vary, the order of dispensation of fluids and beads may vary, and the duration of pauses between each step (if any) may vary. In an embodiment, the user input device 36 and/or the dispenser interface 38 may display one or more images, illustrations, messages, and/or other visual or graphical representations corresponding to an expected outcome hair state that is based upon the formulation recipe.

The product dispensing module 408 instructs the dispenser 34 to dispense a hair formulation made from ingredients of the formulation recipe computed by the formulation module 404. The dispensed ingredients may be dispensed into the mixing area 58. The number of steps in the product dispensing module 408 may vary depending on the formulation recipe, for example depending on the number of beads and fluids in the formulation recipe, and the quantity and volume of each. The product dispensing module 408 may include one or more steps in which the controller 42 instructs at least one bead assembly 46 to dispense one or more beads (e.g., into the mixing area 58), depending on the formulation recipe. The product dispensing module 408 may instruct the bead assembly 46 to dispense beads at more than one rate. For example, if the remaining number of beads for dispensation is below a certain threshold (e.g., is fewer than 10 beads), then the product dispensing module 408 may instruct the bead assembly 46 to run at a relatively low speed to ensure highly accurate dispensation of beads. If the remaining number of beads for dispensation exceeds a threshold (e.g., is at least 10 beads), then the product dispensing module 408 may instruct the bead assembly 46 to run at a relatively high speed to quickly dispense beads. The product dispensing module 408 may utilize one or more sensors (such as load cell 66 or a photocell in the bead assembly 46) to accurately dispense beads and fluids. In an embodiment, the product dispensing module 408 utilizes a load cell to sense a weight of the hair formulation in the mixing area 58 and controls dispensation of the hair formulation based upon the sensed weight.

The product dispensing module 408 may include one or more steps in which the controller 42 may also instruct at least one cartridge assembly 50, pouch assembly 344, or other fluid assembly to dispense one or more volumes of fluids (e.g., into the mixing area 58), depending on the formulation recipe. The controller 42 may automatically trigger the dispensation of one or more beads and/or fluids. In an embodiment, the user may manually trigger the dispensation of one or more beads and/or fluids via the user input device 36 or the dispenser interface 38. For example, the controller 42 may automatically trigger the dispensation of two fluids (e.g., a developer and a diluter), then a user may remove the vessel 262 from the mixing area 58 to manually mix the fluids together before replacing the vessel 262 in the mixing area 58 and manually triggering the dispensation of beads via the dispenser interface 38. A pause of about five seconds to about thirty minutes may precede or follow any of the aforementioned steps of the product dispensing module 408 (whether or not specified by the formulation recipe), e.g., to give one or more beads time to disintegrate. Following the dispensation of all beads and fluids, the dispenser 34 may provide an indication to the user that the dispensation process is complete, e.g., by displaying a message or an icon. This indication may appear as a message on the dispenser interface 38, a sound projected from the dispenser 34, an illuminated light on the dispenser 34, or other indication. In the foregoing description, the order and number of steps can be varied in order to accurately dispense the formulation recipe.

An embodiment of the product dispensing module 408 includes: the controller 42 instructing a first cartridge assembly 50 to dispense a first volume of a first fluid (e.g., a developer); the controller 42 instructing a second cartridge assembly 50 to dispense a second volume of a second fluid (e.g., a diluter); the controller 42 instructing a first bead assembly 46 to dispense a first quantity of a first bead type; the controller 42 instructing a second bead assembly 46 to dispense a second quantity of a second bead type; the controller 42 instructing a third cartridge assembly 50 to dispense a third volume of a third fluid (e.g., a base cream); the controller 42 instructing a fourth cartridge assembly 50 to dispense a fourth volume of a fourth fluid (e.g., a diluter); and the controller 42 instructing a fifth cartridge assembly 50 to dispense a fifth volume of a fifth fluid (e.g., a thickener).

After the product dispensing module 408 dispenses the formulation into the vessel 262, the user may remove the vessel 262 from the mixing area 58, may manually mix the ingredients, and may apply the formulation to the customer's hair.

The inventory monitoring module 412 continuously or periodically monitors the formulation inventory stored in the dispenser 34, including beads stored in bead assemblies 46 and fluids stored in cartridges assemblies 50, pouch assemblies 344, or other fluid containers. For example, the dispenser 34 may monitor whether there is a sufficient supply of beads and/or fluids, whether any beads or fluids are expired, and/or whether any modular bead assemblies 46, modular bead units 190, cartridge assemblies 50, cartridges 54, pouch assemblies 344, and/or pouches 348 are incorrectly installed or inoperative. The dispenser 34 may perform these functions through operative connection between the controller 42, the dispenser interface 38, and the sensors, RFID devices 206, and/or NFC devices in one or more bead assemblies 46, one or more cartridge assemblies 50, and one or more pouch assemblies 344. For example, a bead assembly 46 may be equipped with a photocell. When the bead assembly 46 exhausts its bead supply, the photocell senses the absence of beads and transmits a signal to the controller 42. The bead assembly 46 may also illuminate a light or other visual indicator 138 that may exhibit one or more colors and illumination patterns (e.g., flashing). As another example, when a pouch assembly 344 is empty, a load cell detects that the weight of the formulation in the mixing vessel 332 is constant despite an instruction from the controller to the pouch assembly 344 to dispense fluid; in response, the controller recognizes that the pouch assembly 344 is empty. When the controller 42 receives the signal from the bead assembly 46 or recognizes that pouch assembly 344 is empty, it causes the dispenser interface 38 to indicate that the bead assembly 46 or pouch assembly 344 is empty (e.g., by displaying an error code or a message), and potentially by activating a visual indicator 138 (e.g., a light) located on the bead assembly 46 or pouch assembly 344 at-issue.

In an embodiment of the inventory monitoring module 412, when a modular bead unit 190 is exhausted, the controller 42 instructs the dispenser interface 38 to prompt the user to remove one or more panels or open one or more doors to access the internal space 94 of the dispenser 34. An illuminated light or other visual indicator 138 on the corresponding bead assembly 46 (or cartridge assembly 50 or pouch assembly 344 in other embodiments) then indicates to the user which modular bead unit 190 needs replacing. The user can then remove the exhausted modular bead unit 190, e.g., by pushing against it in embodiments with a push-push latch mechanism, then removing it from the dispenser 34 and replacing it with another.

In an embodiment, the inventory monitoring module 412 validates the replacement modular bead unit(s) 190, cartridge(s) 54, and/or pouch(es) 348 by cross-referencing any RFID or NFC identification signals transmitted by the new modular bead unit(s) 190, cartridge(s) 54, and/or pouch(es) 348 with reference identities stored on the bead assembly 46, cartridge assembly 50, pouch assembly 344, the controller 42, and/or the dispenser interface 38. If one or more of the new RFID or NFC identification signals does not match the corresponding reference identity, it may indicate that the wrong modular bead unit(s) 190, cartridge(s) 54, and/or pouch(es) 348 are installed into the dispenser 34. For example, if a modular bead unit containing purple dye beads is inserted into a bead assembly having a reference corresponding to brown dye beads, then the controller recognizes that the wrong modular bead unit has been installed and causes the dispenser interface to display an error message, and/or activate one or more visual indicators, for example a blinking light or a different color light (e.g., a red light).

The refill module 416 transmits a refill signal to one or more entities (e.g., a distributor, manufacturer, or other supplier) to initiate resupply of modular bead unit(s) 190, cartridge(s) 54, pouch(es) 348, and/or other supply type when the inventory monitoring module 412 detects that a modular bead unit(s) 190, cartridge(s) 54, and/or pouch(es) 348 is exhausted. The reorder message may be automatically transmitted, or manually transmitted at the direction of the user (e.g., via the dispenser interface 38).

The environmental control module 420 controls the climate control system 270 to regulate one or more environmental parameters (e.g., temperature, humidity) within the internal space 94 of the dispenser 34. In particular, the environmental control module 420 may control the climate control system 270 when one or more parameters fall below a predetermined threshold or exceed a predetermined threshold. In an embodiment, the environmental control module 420 includes a preset target temperature range (an upper and/or lower threshold) and a preset target humidity range (an upper and/or lower threshold). In another embodiment, a user may input the target temperature and humidity ranges, e.g., via the dispenser interface 38. Utilizing one or more sensors located in the dispenser 34 (e.g., internal and/or ambient temperature or humidity sensors), the environmental control module 420 determines when to operate the climate control system 270 (e.g., when a sensed humidity level in the dispenser 34 exceeds an upper threshold). In another embodiment, the environmental control module 420 operates the climate control system 270 based upon a timed schedule (e.g., operates the climate control system 270 for five minutes every thirty minutes).

The foregoing modules are merely exemplary. Other embodiments may have additional modules, fewer modules, or different modules.

Generally, connections between operative components of the formulation system 30 may be wired or wireless, and may be direct or indirect. Regardless, any component of the formulation system 30 can be connected to a network that ultimately provides a connection to any other component.

Custom formulation systems disclosed herein utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

In an embodiment of the custom formulation system, circuitry includes one or more ASICs having a plurality of predefined logic components. In an embodiment, circuitry includes one or more FPGA having a plurality of programmable logic components. In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operatively connected via wireless communication. In an embodiment, remotely located components are operatively connected via one or more receivers, transmitters, transceivers, or the like.

In an embodiment, the custom formulation system includes one or more data stores that, for example, store instructions or data. Non-limiting examples of one or more data stores include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more data stores include Erasable Programmable Read-Only Memory (EPROM), flash memory, or the like. The one or more data stores can be connected to, for example, one or more computing devices by one or more instructions, data, or power buses.

In an embodiment, circuitry of the dispensing system includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operatively connected to at least one computing device to control (electrical, electromechanical, software-implemented, firmware-implemented, or other control, or combinations thereof) dispensing of a formulation.

In an embodiment, circuitry of the dispensing system includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are only to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A custom formulation system, comprising:
   a user input device; and
   a dispenser, including:
      a cabinet;
      a bead assembly configured to dispense a plurality of beads containing a first cosmetic formulation, the bead assembly being one of a plurality of bead assemblies located within the cabinet, the plurality of bead assemblies having a vertically organized configuration in which one bead assembly is positioned gravitationally above at least one other bead assembly;
      a fluid formulation assembly configured to dispense a second cosmetic formulation in flowable fluid form, the fluid formulation assembly being one of a plurality of fluid formulation assemblies located within the cabinet; and
      a mixing area located within the cabinet and configured to receive at least one bead from the bead assembly and the second cosmetic formulation in flowable fluid form from the fluid formulation assembly,
      wherein the plurality of vertically organized bead assemblies, the plurality of fluid formulation assemblies, and the mixing area are positioned adjacent to a first side of the cabinet.

2. The custom formulation system of claim 1, wherein the bead assembly includes a modular bead unit containing the plurality of beads, the modular bead unit being configured for removable attachment with the bead assembly without tools.

3. The custom formulation system of claim 1, wherein the bead assembly is configured for removable attachment with the dispenser without tools.

4. The custom formulation system of claim 1, wherein one bead assembly is positioned gravitationally above at least two other bead assemblies.

5. The custom formulation system of claim 4, wherein the plurality of bead assemblies also has a horizontal configuration.

6. The custom formulation system of claim 1, wherein the plurality of fluid formulation assemblies has a horizontally organized configuration.

7. The custom formulation system of claim 1, wherein the fluid formulation assembly is configured to receive one of a cartridge containing the second cosmetic formulation or a pouch containing the second cosmetic formulation.

8. The custom formulation system of claim 1, wherein the fluid formulation assembly is configured for removal and attachment with the dispenser without tools.

9. The custom formulation system of claim 1, wherein the dispenser further comprises a chute between the bead assembly and the mixing area.

10. The custom formulation system of claim 9, wherein the chute is configured to transport beads from a plurality of bead assemblies.

11. The custom formulation system of claim 1, wherein the bead assembly is one of a plurality of bead assemblies and the fluid formulation assembly is one of a plurality of fluid formulation assemblies.

12. The custom formulation system of claim 10, wherein each bead assembly and fluid formulation assembly are arranged in the dispenser in a common plane.

13. The custom formulation system of claim 1, further comprising a controller operatively connectable with: the user input device, the bead assembly, and the fluid formulation assembly, the controller being configured to: receive information from the user input device, instruct the bead assembly to dispense at least one bead, and instruct the fluid formulation assembly to dispense the second cosmetic formulation.

14. The custom formulation system of claim 13, wherein the dispenser further comprises a climate control system operatively connected to the controller.

15. The custom formulation system of claim 1, wherein the user input device is integral with dispenser.

16. The custom formulation system of claim 1, wherein the bead assembly, fluid formulation assembly, and mixing area are contained within the dispenser.

17. The custom formulation system of claim 1, further comprising a tube configured to transfer fluid from the fluid formulation assembly to the mixing area.

18. The custom formulation system of claim 13, wherein the controller includes a processor and logic that, when executed, causes the system to perform operations including:
   computing a target cosmetic formulation recipe based upon the information received from the user input device;
   dispensing a quantity of cosmetic formulation beads from the bead assembly, the quantity of cosmetic formulation beads being based upon the target cosmetic formulation recipe; and
   dispensing a volume of the second cosmetic formulation from fluid formulation assembly, the volume being based upon the target cosmetic formulation recipe.

19. The custom formulation system of claim 18, wherein the controller further includes logic that, when executed by the processor, cause at least one of the user input device or the dispenser to issue a notification when a bead supply of the bead assembly falls below a first threshold or when a fluid supply of the fluid formulation assembly falls below a second threshold.

20. A custom formulation dispenser, comprising:
   a cabinet;
   a bead assembly configured to dispense a plurality of beads containing a first cosmetic formulation, the bead assembly being one of a plurality of bead assemblies located within the cabinet, the plurality of bead assemblies having a vertically organized configuration in which one bead assembly is positioned gravitationally above at least one other bead assembly;
   a fluid formulation assembly configured to dispense a second cosmetic formulation in flowable fluid form, the fluid formulation assembly being one of a plurality of fluid formulation assemblies located within the cabinet; and
   a mixing area located within the cabinet and configured to receive at least one bead from the bead assembly and the second cosmetic formulation in flowable fluid form from the fluid formulation assembly,
   wherein the plurality of vertically organized bead assemblies, the plurality of fluid formulation assemblies, and the mixing area are positioned adjacent to a first side of the cabinet.

* * * * *